US011535876B2

(12) United States Patent
Xie et al.

(10) Patent No.: US 11,535,876 B2
(45) Date of Patent: Dec. 27, 2022

(54) XYLOSE-INDUCED GENETICALLY ENGINEERED BACTERIA USED FOR PRODUCING ECTOINE AND USE THEREOF

(71) Applicant: Tianjin University of Science and Technology, Tianjin (CN)

(72) Inventors: Xixian Xie, Tianjin (CN); Xuejiao Wu, Tianjin (CN); Ning Chen, Tianjin (CN); Fangqing Yan, Tianjin (CN); Qian Ma, Tianjin (CN); Jie Ma, Tianjin (CN); Hongchao Zhang, Tianjin (CN)

(73) Assignee: Tianjin University of Science and Technology, Tianjin (CN)

( * ) Notice: Subject to any disclaimer, the term of this patent is extended or adjusted under 35 U.S.C. 154(b) by 173 days.

(21) Appl. No.: 15/759,833

(22) PCT Filed: Jun. 14, 2017

(86) PCT No.: PCT/CN2017/088284
§ 371 (c)(1),
(2) Date: Mar. 14, 2018

(87) PCT Pub. No.: WO2018/126610
PCT Pub. Date: Jul. 12, 2018

(65) Prior Publication Data
US 2022/0186271 A1    Jun. 16, 2022

(30) Foreign Application Priority Data
Jan. 9, 2017    (CN) .......................... 201710012845.6

(51) Int. Cl.
*C12P 17/12*    (2006.01)
*C12N 9/04*    (2006.01)
*C12N 9/10*    (2006.01)
*C12N 9/12*    (2006.01)
*C12N 9/88*    (2006.01)

(52) U.S. Cl.
CPC ............ *C12P 17/12* (2013.01); *C12N 9/0006* (2013.01); *C12N 9/1029* (2013.01); *C12N 9/1096* (2013.01); *C12N 9/127* (2013.01); *C12N 9/1217* (2013.01); *C12N 9/88* (2013.01); *C12Y 101/01003* (2013.01); *C12Y 203/01178* (2013.01); *C12Y 206/01076* (2013.01); *C12Y 207/02004* (2013.01); *C12Y 207/07048* (2013.01); *C12Y 401/01031* (2013.01); *C12Y 402/01108* (2013.01)

(58) Field of Classification Search
None
See application file for complete search history.

(56) References Cited

U.S. PATENT DOCUMENTS

2003/0166054 A1* 9/2003 Lee .................. C12N 15/67
                                                    435/69.1
2011/0300576 A1* 12/2011 Barnes .................. C12N 15/63
                                                    435/320.1

FOREIGN PATENT DOCUMENTS

| CN | 104560844 A | 4/2015 | |
|---|---|---|---|
| CN | 104593442 A | 5/2015 | |
| CN | 105018403 A | 11/2015 | |
| CN | 105177078 A | 12/2015 | |
| CN | 105669560 A | 6/2016 | |
| CN | 106754603 A | 5/2017 | |
| KR | 20110052343 A | * 5/2011 | ............. C12N 15/70 |

OTHER PUBLICATIONS

Nakashima et al., Establishment of a novel gene expression method, BICES, biomass-inducible chromosome-based expression system, and its application to the production of 2,3-butanediolandacetoin, Metabolic Eng. 25, 2014, 204-14. (Year: 2014).*
Amann et al.,Tightly regulated tac promoter vectors useful for the expression of unfused and fused proteins in *Escherichia coli*, Gene 69, 1988, 301-15. (Year: 1988).*
Lee et al., Systems metabolic engineering of *Escherichia coli* for L-threonine production, Molecular Syst. Biol. 3, 2007, 149. (Year: 2007).*
Machine translation of CN 105018403 A, 2015. (Year: 2015).*
Ning et al., Pathway construction and metabolic engineering for fermentative production of ectoine in *Escherichia coli*, Metabolic Eng. 36 (2016): 10-18. (Year: 2016).*
Characterization and phylogenetic analysis of ectoine biosynthesis genes from Bacillus halodurans, «Archives of Microbiology» , Jul. 16, 2008.

(Continued)

*Primary Examiner* — Robert B Mondesi
*Assistant Examiner* — Todd M Epstein
(74) *Attorney, Agent, or Firm* — Bayramoglu Law Offices LLC

(57) ABSTRACT

The present disclosure relates to the field of genetic engineering, especially relates to a xylose-induced genetically engineered bacteria used for producing ectoine as well as a construction method and use thereof. The genetically engineered bacteria is constructed by heterologously expressing the ectABC gene cluster from *Halomonas elongata* on the *E. coli* chromosome, using the promoter of xylose transporter coding gene xylF to control the RNA polymerase from T7 bacteriophage, reconstructing a synthesis pathway of ectoine and constructing a plasmid-free system, and enhancing the expression of target genes by a strong promoter T7; the yield of ectoine reached 12-16 g/L after 20-28 h fermentation in shake flask, and reached 35-50 g/L after 24-40 h fermentation in a 5 L fermentor.

9 Claims, 2 Drawing Sheets

Specification includes a Sequence Listing.

(56) References Cited

OTHER PUBLICATIONS

Osmotically induced synthesis of the compatible solute hydroxyectoine is mediated by an evolutionarily conserved ectoine hydroxylase, <<The Journal of Biological Chemistry>>, Nov. 26, 2007.
Pathway construction and metabolic engineering for fermentative production of ectoine in *Escherichia coli*, Mar. 9, 2016, Yike Ning, Xuejiao Wu, Chenglin Zhang, Qingyang Xu, Ning Chen, Xixian Xie.

* cited by examiner

SEQUENCE LISTING

```
<160> NUMBER OF SEQ ID NOS: 58

<210> SEQ ID NO 1
<211> LENGTH: 2259
<212> TYPE: DNA
<213> ORGANISM: Artificial sequence
<220> FEATURE:
<223> OTHER INFORMATION: Halomonas elongata CGMCC 1.6329

<400> SEQUENCE: 1
atgaacgcaa ccacagagcc ctttacaccc tccgccgacc tggccaagcc cagcgtggcc      60
gatgccgtgg tcggccatga ggcctcaccg ctcttcatcc gcaagccaag ccccgatgac     120
ggctggggca tctacgagct ggtcaagtcc tgtccgcctc tcgacgtcaa ttccgcctac     180
gcctatctgt tgctggccac ccagttccgc gatagctgcg ccgtggcgac caacgaagag     240
ggcgagatcg tcggcttcgt ttccggctac gtgaagagca acgcccccga tacctatttc     300
ctctggcagg ttgccgtggg cgagaaggca cgtggcaccg gcctggcccg tcgtctggtg     360
gaagccgtga tgacacgccc ggaaatggcc gaggtccacc atctcgagac cactatcacg     420
cccgacaacc aggcgtcctg gggcttgttc cgccgtctcg ccgatcgctg gcaggcgccg     480
ttgaacagcc gcgaatactt ctccaccgat caactcggcg gtgagcatga cccggaaaac     540
ctcgttcgca tcggcccgtt ccagaccgac cagatctgaa tgcagaccca gattctcgaa     600
cgcatggagt ccgacgttcg gacctactcc cgctccttcc cggtcgtctt caccaaggcg     660
cgcaatgccc gcctgaccga cgaggaaggg cgcgagtaca tcgacttcct ggccggtgcc     720
ggcaccctga actacggcca caacaaccog cacctcaagc aggcgctgct cgactatatc     780
gacagcgacg gcatcgtcca cggcctggac ttctggactg cggccaagcg cgactatctg     840
gaaaccctgg aagaggtgat cctcaagccg cgcggtctcg actacaaggt gcatctgccc     900
ggaccgactg gcaccaacgc cgtcgaggcg gccattcgcc tggcccgggt cgccaagggg     960
cgccacaata tcgtctcctt caccaacggc tttcatggcg tcaccatggg cgcgctggcg    1020
accaccggta accgcaagtt ccgcgaggcc accggtggcg tgccgaccca ggctgcttcc    1080
ttcatgccgt tcgatggcta cctcggcagc agcaccgaca ccctcgacta cttcgagaag    1140
ctgctcggcg acaagtccgg cggcctggac gtgcccgcgg cggtgatcgt cgagacagtg    1200
cagggcgagg gcggtatcaa tgtcgccggc ctggagtggc tcaagcgcct cgagagcatc    1260
tgccgcgcca atgacatcct gctgatcatc gacgacatcc aggcgggctg cggccggacc    1320
ggcaagttct tcagcttcga gcatgccggc atcacgccgg atatcgtgac caactccaag    1380
tcgctgtccg gttacggcct gccgttcgct cacgtcctga tgcgccccga gctcgacaag    1440
tggaagcccg gtcagtacaa cggcaccttc gcggcttca acctggcttt cgccactgct    1500
gctgccgcca tgcgcaagta ctggagcgac gacaccttcg agcgtgacgt gcagcgcaag    1560
gctcgcatcg tcgaggaacg cttcggcaag atcgccgcct ggctgagcga aacggcatc    1620 gaggcctccg agcgcggccg cgggctgatg cggggcatcg acgtgggttc cggcgatatc    1680
gccgacaaga tcccccacca agccttcgag aacgggttga tcatcgaaac cagcggtcag    1740
gacggcgaag tggtcaagtg cctgtgcccg ctgaccattc ccgacgaaga cctggtcgag    1800
```

```
ggactcgaca tcctcgagac cagcaccaag caggccttta gctgaatgat cgttcgcaat    1860
ctcgaagaag cgcgccagac cgaccgtctg gtcaccgccg aaaacggcaa ctgggacagc    1920
acccgcctgt cgctggccga agatggtggc aactgctcct tccacatcac ccgcatcttc    1980
gagggtaccg agaccacat ccactataag catcacttcg aggctgttta ttgcatcgaa     2040
ggcgagggcg aagtggaaac cctggccgat ggcaagatct ggcccatcaa gccgggtgac    2100
atctacatcc tcgaccagca cgacgagcac ctgctgcgcg ccagcaagac catgcacctg    2160
gcctgcgtgt tcacgccggg cctgaccggc aacgaagtgc accgcgaaga cggttcctac    2220
gcacctgccg acgaagccga cgaccagaag ccgctgtaa                           2259
```

<210> SEQ ID NO 2
<211> LENGTH: 1266
<212> TYPE: DNA
<213> ORGANISM: Artificial sequence
<220> FEATURE:
<223> OTHER INFORMATION: Corynebacterium glutamicum ATCC13032

<400> SEQUENCE: 2

```
gtggccctgg tcgtacagaa atatggcggt tcctcgcttg agagtgcgga acgcattaga     60
aacgtcgctg aacggatcgt tgccaccaag aaggctggaa atgatgtcgt ggttgtctgc    120
tccgcaatgg gagacaccac ggatgaactt ctagaacttg cagcggcagt gaatcccgtt    180
ccgccagctc gtgaaatgga tatgctcctg actgctggtg agcgtatttc taacgctctc    240
gtcgccatgg ctattgagtc ccttggcgca gaagcccaat cttcacggg ctctcaggct      300 ggtgtgctca ccaccgagcg ccacggaaac gcacgcattg ttgatgtcac tccaggtcgt    360
gtgcgtgaag cactcgatga gggcaagatc tgcattgttg ctggtttcca gggtgttaat    420
aaagaaaccc gcgatgtcac cacgttgggt cgtggtggtt ctgacaccac tgcagttgcg    480
ttggcagctg cttttgaacgc tgatgtgtgt gagatttact cggacgttga cggtgtgtat    540
accgctgacc cgcgcatcgt tcctaatgca cagaagctgg aaaagctcag cttcgaagaa    600
atgctggaac ttgctgctgt tggctccaag attttggtgc tgcgcagtgt tgaatacgct    660
cgtgcattca atgtgccact tcgcgtacgc tcgtcttata gtaatgatcc cggcactttg    720
attgccggct ctatggagga tattcctgtg gaagaagcag tccttaccgg tgtcgcaacc    780
gacaagtccg aagccaaagt aaccgttctg ggtatttccg ataagccagg cgaggctgcg    840
aaggttttcc gtgcgttggc tgatgcagaa atcaacattg acatggttct gcagaacgtc    900
tcttctgtag aagacggcac caccgacatc accttcacct gccctcgttc cgacggccgc    960
cgcgcgatgg agatcttgaa gaagcttcag gttcagggca actggaccaa tgtgctttac   1020
gacgaccagg tcggcaaagt ctccctcgtg ggtgctggca tgaagtctca cccaggtgtt   1080
accgcagagt tcatggaagc tctgcgcgat gtcaacgtga acatcgaatt gatttccacc   1140
tctgagattc gtatttccgt gctgatccgt gaagatgatc tggatgctgc tgcacgtgca   1200
ttgcatgagc agttccagct gggcggcgaa gacgaagccg tcgtttatgc aggcaccgga   1260
cgctaa                                                              1266
```

<210> SEQ ID NO 3
<211> LENGTH: 2463
<212> TYPE: DNA
<213> ORGANISM: Artificial sequence
<220> FEATURE:
<223> OTHER INFORMATION: E. coli W3110ATCC 27325

<400> SEQUENCE: 3

```
atgcgagtgt tgaagttcgg cggtacatca gtggcaaatg cagaacgttt tctgcgtgtt      60
gccgatattc tggaaagcaa tgccaggcag gggcaggtgg ccaccgtcct ctctgccccc     120
gccaaaatca ccaaccacct ggtggcgatg attgaaaaaa ccattagcgg ccaggatgct     180
ttacccaata tcagcgatgc cgaacgtatt tttgccgaac ttttgacggg actcgccgcc     240
gcccagccgg ggttcccgct ggcgcaattg aaaactttcg tcgatcagga atttgcccaa     300
ataaaacatg tcctgcatgg cattagtttg ttggggcagt gcccggatag catcaacgct     360
gcgctgattt gccgtggcga gaaaatgtcg atcgccatta tggccggcgt attagaagcg     420
cgcggtcaca acgttactgt tatcgatccg gtcgaaaaac tgctggcagt ggggcattac     480
ctcgaatcta ccgtcgatat tgctgagtcc accgccgta ttgcggcaag ccgcattccg     540
gctgatcaca tggtgctgat ggcaggtttc accgccggta atgaaaaagg cgaactggtg     600
gtgcttggac gcaacggttc cgactactct gctgcggtgc tggctgcctg tttacgcgcc     660
gattgttgcg agatttggac ggacgttgac ggggtctata cctgcgaccc gcgtcaggtg     720
cccgatgcga ggttgttgaa gtcgatgtcc taccaggaag cgatggagct ttcctacttc     780
ggcgctaaag ttcttcaccc ccgcaccatt accccatcg cccagttcca gatcccttgc     840
ctgattaaaa ataccggaaa tcctcaagca ccaggtacgc tcattggtgc cagccgtgat     900
gaagacgaat accggtcaa gggcatttcc aatctgaata acatggcaat gttcagcgtt     960
tctggtccgg ggatgaaagg gatggtcggc atggcggcgc gcgtctttgc agcgatgtca    1020
cgcgcccgta tttccgtggt gctgattacg caatcatctt ccgaatacag catcagtttc    1080
tgcgttccac aaagcgactg tgtgcgagct gaacgggcaa tgcaggaaga gttctacctg    1140
gaactgaaag aaggcttact ggagccgctg gcagtgacgg aacggctggc cattatctcg    1200
gtggtaggtg atggtatgcg caccttgcgt gggatctcgg cgaaattctt tgccgcactg    1260
gcccgcgcca atatcaacat tgtcgccatt gctcagggat cttctgaacg ctcaatctct    1320
gtcgtggtaa ataacgatga tgcgaccact ggcgtgcgcg ttactcatca gatgctgttc    1380
aataccgatc aggttatcga agtgtttgtg attggcgtcg gtggcgttgg cggtgcgctg    1440
ctggagcaac tgaagcgtca gcaaagctgg ctgaagaata acatatcga cttacgtgtc    1500
tgcggtgttg ccaactcgaa ggctctgctc accaatgtac atggccttaa tctgaaaaac    1560
tggcaggaag aactggcgca agccaaagag ccgtttaatc tcgggcgctt aattcgcctc    1620
gtgaaagaat atcatctgct gaacccggtc attgttgact gcacttccag ccaggcagtg    1680
gcggatcaat atgccgactt cctgcgcgaa ggtttccacg ttgtcacgcc gaacaaaaag    1740
gccaacacct cgtcgatgga ttactaccat cagttgcgtt atgcggcgga aaaatcgcgg    1800
cgtaaattcc tctatgacac caacgttggg gctggattac cggttattga gaacctgcaa    1860
aatctgctca atgcaggtga tgaattgatg aagttctccg gcattctttc tggttcgctt    1920
tcttatatct tcggcaagtt agacgaaggc atgagtttct ccgaggcgac cacgctggcg    1980
cgggaaatgg ttataccgga accggacccg cgagatgatc tttctggtat ggatgtggcg    2040
cgtaaactat tgattctcgc tcgtgaaacg ggacgtgaac tggagctggc ggatattgaa    2100
attgaacctg tgctgccgc agagtttaac gccgagggtg atgttgccgc ttttatggcg    2160
aatctgtcac aactcgacga tctctttgcc gcgcgcgtgg cgaaggcccg tgatgaagga    2220
aaagttttgc gctatgttgg caatattgat gaagatggcg tctgccgcgt gaagattgcc    2280
gaagtggatg gtaatgatcc gctgttcaaa gtgaaaaatg gcgaaaacgc cctggccttc    2340
```

-continued

| | |
|---|---|
| tatagccact attatcagcc gctgccgttg gtactgcgcg gatatggtgc gggcaatgac | 2400 |
| gttacagctg ccggtgtctt tgctgatctg ctacgtaccc tctcatggaa gttaggagtc | 2460 |
| tga | 2463 |

<210> SEQ ID NO 4
<211> LENGTH: 825
<212> TYPE: DNA
<213> ORGANISM: Artificial sequence
<220> FEATURE:
<223> OTHER INFORMATION: E. coli W3110ATCC 27325

<400> SEQUENCE: 4

| | |
|---|---|
| atggtcgcac ccattcccgc gaaacgcggc agaaaacccg ccgttgccac cgcaccagcg | 60 |
| actggacagg ttcagtcttt aacgcgtggc ctgaaattac tggagtggat tgccgaatcc | 120 |
| aatggcagtg tggcactcac ggaactggcg caacaagccg ggttacccaa ttccacgacc | 180 |
| caccgcctgc taaccacgat gcaacagcag ggtttcgtgc gtcaggttgg cgaactggga | 240 |
| cattgggcaa tcggcgcaca tgcctttatg gtcggcagca gctttctcca gagccgtaat | 300 |
| ttgttagcga ttgttcaccc tatcctgcgc aatctaatgg aagagtctgg cgaaacggtc | 360 |
| aatatggcgg tgcttgatca aagcgatcac gaagcgatta ttatcgacca ggtacagtgt | 420 |
| acgcatctga tgcgaatgtc cgcgcctatc ggcgtaaat tgccgatgca cgcttccggt | 480 |
| gcgggtaaag cctttttagc ccaactgagc gaagaacagg tgacgaagct gctgcaccgc | 540 |
| aaagggttac atgcctatac ccacgcaacg ctggtgtctc ctgtgcattt aaaagaagat | 600 |
| ctcgcccaaa cgcgcaaacg gggttattca tttgacgatg aggaacatgc actggggcta | 660 |
| cgttgccttg cagcgtgtat tttcgatgag caccgtgaac cgtttgccgc aatttctatt | 720 |
| tccggaccga tttcacgtat taccgatgac cgcgtgaccg agtttggcgc gatggtgatt | 780 |
| aaagcggcga aggaagtgac gctggcgtac ggtggaatgc gctga | 825 |

<210> SEQ ID NO 5
<211> LENGTH: 19
<212> TYPE: DNA
<213> ORGANISM: Artificial sequence
<220> FEATURE:
<223> OTHER INFORMATION: pET-his

<400> SEQUENCE: 5

| | |
|---|---|
| taatacgact cactatagg | 19 |

<210> SEQ ID NO 6
<211> LENGTH: 48
<212> TYPE: DNA
<213> ORGANISM: Artificial sequence
<220> FEATURE:
<223> OTHER INFORMATION: pET-his

<400> SEQUENCE: 6

| | |
|---|---|
| ctagcataac cccttggggc ctctaaacgg gtcttgaggg gttttttg | 48 |

<210> SEQ ID NO 7
<211> LENGTH: 30
<212> TYPE: DNA
<213> ORGANISM: Artificial sequence
<220> FEATURE:
<223> OTHER INFORMATION: ptrc99a plasmid

<400> SEQUENCE: 7

-continued ttgacaatta atcatccggc tcgtataatg        30

<210> SEQ ID NO 8
<211> LENGTH: 2652
<212> TYPE: DNA
<213> ORGANISM: Artificial sequence
<220> FEATURE:
<223> OTHER INFORMATION: E. coli W3110ATCC 27325

<400> SEQUENCE: 8

| | |
|---|---|
| atgaacgaac aatattccgc attgcgtagt aatgtcagta tgctcggcaa agtgctggga | 60 |
| gaaaccatca aggatgcgtt gggagaacac attcttgaac gcgtagaaac tatccgtaag | 120 |
| ttgtcgaaat cttcacgcgc tggcaatgat gctaaccgcc aggagttgct caccacctta | 180 |
| caaaatttgt cgaacgacga gctgctgccc gttgcgcgtg cgtttagtca gttcctgaac | 240 |
| ctggccaaca ccgccgagca ataccacagc atttcgccga aggcgaagc tgccagcaac | 300 |
| ccggaagtga tcgcccgcac cctgcgtaaa ctgaaaaacc agccggaact gagcgaagac | 360 |
| accatcaaaa aagcagtgga atcgctgtcg ctggaactgg tcctcacggc tcacccaacc | 420 |
| gaaattaccc gtcgtacact gatccacaaa atggtggaag tgaacgcctg tttaaaacag | 480 |
| ctcgataaca aagatatcgc tgactacgaa cacaaccagc tgatgcgtcg cctgcgccag | 540 |
| ttgatcgccc agtcatggca taccgatgaa atccgtaagc tgcgtccaag cccggtagat | 600 |
| gaagccaaat ggggctttgc cgtagtgaa acagcctgt ggcaaggcgt accaaattac | 660 |
| ctgcgcgaac tgaacgaaca actggaagag aacctcggct acaaactgcc cgtcgaattt | 720 |
| gttccggtcc gttttacttc gtggatgggc ggcaccgcg acggcaaccc gaacgtcact | 780 |
| gccgatatca cccgccacgt cctgctactc agccgctgga agccaccga tttgttcctg | 840 |
| aaagatattc aggtgctggt ttctgaactg tcgatggttg aagcgacccc tgaactgctg | 900 |
| gcgctggttg gcgaagaagg tgccgcagaa ccgtatcgct atctgatgaa aaacctgcgt | 960 |
| tctcgcctga tggcgacaca ggcatggctg gaagcgcgcc tgaaaggcga agaactgcca | 1020 |
| aaaccagaag gcctgctgac acaaaacgaa gaactgtggg aaccgctcta cgcttgctac | 1080 |
| cagtcacttc aggcgtgtgg catgggtatt atcgccaacg cgatctgct cgacaccctg | 1140 |
| cgccgcgtga atgtttcgg cgtaccgctg gtccgtattg atatccgtca ggagagcacg | 1200 |
| cgtcataccg aagcgctggg cgagctgacc cgctacctcg gtatcggcga ctacgaaagc | 1260 |
| tggtcagagg ccgacaaaca ggcgttcctg atccgcgaac tgaactccaa acgtccgctt | 1320 |
| ctgccgcgca actggcaacc aagcgccgaa acgcgcgaag tgctcgatac ctgccaggtg | 1380 |
| attgccgaag caccgcaagg ctccattgcc gcctacgtga tctcgatggc gaaaacgccg | 1440 |
| tccgacgtac tggctgtcca cctgctgctg aaagaagcgg gtatcgggtt tgcgatgccg | 1500 |
| gttgctccgc tgtttgaaac cctcgatgat ctgaacaacg ccaacgatgt catgacccag | 1560 |
| ctgctcaata ttgactggta tcgtggcctg attcagggca acagatggt gatgattggc | 1620 |
| tattccgact cagcaaaaga tgcgggagtg atggcagctt cctgggcgca atatcaggca | 1680 |
| caggatgcat taatcaaaac ctgcgaaaaa gcgggtattg agctgacgtt gttccacggt | 1740 |
| cgcggcggtt ccattggtcg cggcggcgca cctgctcatg cggcgctgct gtcacaaccg | 1800 |
| ccaggaagcc tgaaaggcgg cctgcgcgta accgaacagg gcgagatgat ccgctttaaa | 1860 |
| tatggtctgc cagaaatcac cgtcagcagc ctgtcgcttt ataccggggc gattctggaa | 1920 |
| gccaacctgc tgccaccgcc ggagccgaaa gagagctggc gtcgcattat ggatgaactg | 1980 |
| tcagtcatct cctgcgatgt ctaccgcggc tacgtacgtg aaaacaaaga ttttgtgcct | 2040 |

```
tacttccgct ccgctacgcc ggaacaagaa ctgggcaaac tgccgttggg ttcacgtccg    2100
gcgaaacgtc gcccaaccgg cggcgtcgag tcactacgcg ccattccgtg gatcttcgcc    2160
tggacgcaaa accgtctgat gctccccgcc tggctgggtg caggtacggc gctgcaaaaa    2220
gtggtcgaag acggcaaaca gagcgagctg gaggctatgt gccgcgattg gccattcttc    2280
tcgacgcgtc tcggcatgct ggagatggtc ttcgccaaag cagacctgtg gctggcggaa    2340
tactatgacc aacgcctggt agacaaagca ctgtggccgt taggtaaaga gttacgcaac    2400
ctgcaagaag aagacatcaa agtggtgctg gcgattgcca acgattccca tctgatggcc    2460
gatctgccgt ggattgcaga gtctattcag ctacggaata tttacaccga cccgctgaac    2520
gtattgcagg ccgagttgct gcaccgctcc cgccaggcag aaaagaagg ccaggaaccg    2580 gatcctcgcg tcgaacaagc gttaatggtc actattgccg ggattgcggc aggtatgcgt    2640
aataccggct aa                                                       2652

<210> SEQ ID NO 9
<211> LENGTH: 268
<212> TYPE: DNA
<213> ORGANISM: Artificial sequence
<220> FEATURE:
<223> OTHER INFORMATION: E. coli W3110ATCC 27325

<400> SEQUENCE: 9
gagataattc acaagtgtgc gctcgctcgc aaaataaaat ggaatgatga aactgggtaa      60
ttcctcgaag agaaaaatgc aataagtaca attgcgcaac aaaagtaaga tctcggtcat    120
aaatcaagaa ataaaccaaa aatcgtaatc gaaagataaa aatctgtaat tgttttcccc    180
tgtttagttg ctaaaaattg gttacgttta tcgcggtgat tgttacttat taaaactgtc    240
ctctaactac agaaggccct acaccatg                                       268

<210> SEQ ID NO 10
<211> LENGTH: 2652
<212> TYPE: DNA
<213> ORGANISM: Artificial sequence
<220> FEATURE:
<223> OTHER INFORMATION: E. coli BL21(DE3)

<400> SEQUENCE: 10
atgaacacga ttaacatcgc taagaacgac ttctctgaca tcgaactggc tgctatcccg     60
ttcaacactc tggctgacca ttacggtgag cgtttagctc gcgaacagtt ggcccttgag    120
catgagtctt acgagatggg tgaagcacgc ttccgcaaga tgtttgagcg tcaacttaaa    180
gctggtgagg ttgcggataa cgctgccgcc aagcctctca tcactaccct actccctaag    240
atgattgcac gcatcaacga ctggtttgag gaagtgaaag ctaagcgcgg caagcgcccg    300
acagccttcc agttcctgca agaaatcaag ccggaagccg tagcgtacat caccattaag    360
accactctgg cttgcctaac cagtgctgac aatacaaccg ttcaggctgt agcaagcgca    420
atcggtcggg ccattgagga cgaggctcgc ttcggtcgta tccgtgacct tgaagctaag    480
cacttcaaga aaaacgttga ggaacaactc aacaagcgcg tagggcacgt ctacaagaaa    540
gcatttatgc aagttgtcga ggctgacatg ctctctaagg gtctactcgg tggcgaggcg    600
tggtcttcgt ggcataagga agactctatt catgtaggag tacgctgcat cgagatgctc    660
attgagtcaa ccggaatggt tagcttacac cgccaaaatg ctggcgtagt aggtcaagac    720
tctgagacta tcgaactcgc acctgaatac gctgaggcta tcgcaacccg tgcaggtgcg    780
```

```
ctggctggca tctctccgat gttccaacct tgcgtagttc ctcctaagcc gtggactggc      840
attactggtg gtggctattg ggctaacggt cgtcgtcctc tggcgctggt gcgtactcac      900
agtaagaaag cactgatgcg ctacgaagac gtttacatgc ctgaggtgta caaagcgatt      960
aacattgcgc aaaacaccgc atggaaaatc aacaagaaag tcctagcggt cgccaacgta     1020
atcaccaagt ggaagcattg tccggtcgag acatccctg cgattgagcg tgaagaactc      1080
ccgatgaaac cggaagacat cgacatgaat cctgaggctc tcaccgcgtg aaacgtgct      1140 gccgctgctg tgtaccgcaa ggacaaggct cgcaagtctc gccgtatcag ccttgagttc     1200
atgcttgagc aagccaataa gtttgctaac cataaggcca tctggttccc ttacaacatg     1260
gactggcgcg gtcgtgttta cgctgtgtca atgttcaacc cgcaaggtaa cgatatgacc     1320
aaaggactgc ttacgctggc gaaaggtaaa ccaatcggta aggaaggtta ctactggctg     1380
aaaatccacg gtgcaaactg tgcgggtgtc gataaggttc cgttccctga gcgcatcaag     1440
ttcattgagg aaaaccacga gaacatcatg gcttgcgcta agtctccact ggagaacact     1500
tggtgggctg agcaagattc tccgttctgc ttccttgcgt tctgctttga gtacgctggg     1560
gtacagcacc acggcctgag ctataactgc tcccttccgc tggcgtttga cgggtcttgc     1620
tctggcatcc agcacttctc cgcgatgctc cgagatgagg taggtggtcg cgcggttaac     1680
ttgcttccta gtgaaaccgt tcaggacatc tacgggattg ttgctaagaa agtcaacgag     1740
attctacaag cagacgcaat caatgggacc gataacgaag tagttaccgt gaccgatgag     1800
aacactggtg aaatctctga gaaagtcaag ctgggcacta aggcactggc tggtcaatgg     1860
ctggcttacg tgttactcg cagtgtgact aagcgttcag tcatgacgct ggcttacggg     1920
tccaaagagt tcggcttccg tcaacaagtg ctggaagata ccattcagcc agctattgat     1980
tccggcaagg gtctgatgtt cactcagccg aatcaggctg ctggatacat ggctaagctg     2040
atttgggaat ctgtgagcgt gacggtggta gctgcggttg aagcaatgaa ctggcttaag     2100
tctgctgcta agctgctggc tgctgaggtc aaagataaga agactggaga gattcttcgc     2160
aagcgttgcg ctgtgcattg ggtaactcct gatggtttcc ctgtgtggca ggaatacaag     2220
aagcctattc agacgcgctt gaacctgatg ttcctcggtc agttccgctt acagcctacc     2280
attaacacca acaaagatag cgagattgat gcacacaaac aggagtctgg tatcgctcct     2340
aactttgtac acagccaaga cggtagccac cttcgtaaga ctgtagtgtg gcacacgag      2400 aagtacggaa tcgaatcttt tgcactgatt cacgactcct tcggtaccat tccggctgac     2460
gctgcgaacc tgttcaaagc agtgcgcgaa actatggttg acacatatga gtcttgtgat     2520
gtactggctg atttctacga ccagttcgct gaccagttgc acgagtctca attggacaaa     2580
atgccagcac ttccggctaa aggtaacttg aacctccgtg acatcttaga gtcggacttc     2640
gcgttcgcgt aa                                                         2652

<210> SEQ ID NO 11
<211> LENGTH: 788
<212> TYPE: DNA
<213> ORGANISM: Artificial sequence
<220> FEATURE:
<223> OTHER INFORMATION: E. coli W3110ATCC 27325

<400> SEQUENCE: 11
atgctggttg ccgcaggaca gtttgctgtt acatctgtgt gggaaaagaa cgctgagatt        60
tgtgcctcgt tgatgcgca ggcggcgaa aacgacgcat cgctgtttgc cctgccggaa        120
gcattgctgg cgcgcgatga tcatgatgca gatctatcgg ttaaatcagc acagctgctg      180
```

```
gaaggcgaat tcctcggact ttacggcgag aaagtaaacg taacatgatg acgacaattc    240
tgacgattca tgttccttca acgccggggc gcgcatggaa tatgctggtg cacttcagg     300 caggaaacat cgtcgcccgt tatgccaaac tgcatctcta tgatgcattt gccattcagg    360
aatcacgccg tgttgatgct ggtaatgaaa tcgctccgtt actggagtg gaagggatga     420 aggtcggtct gatgacctgt tatgacttac gctttccaga gctggcgctg gcacaggcat    480
tacagggagc tgaaatcctg gtacttcctg ccgcctgggt tcgcgggccg ctcaaagagc    540
atcactggtc aacgttgctt gccgctcgtg cgctggatac cacctgttat atggtggcgg    600
cgggggagtg cggaacaaa aatatcggtc aaagccggat tatagatccc tttggcgtca     660
ccattgcggc agcgtcagaa atgcctgcac tcattatggc ggaagtgacg cccgaacgtg    720
tgcgtcaggt gcgcgcgcaa ctgcccgtct aaacaaccg tcgctttgcg ccgccgcaat     780
tattatga                                                            788

<210> SEQ ID NO 12
<211> LENGTH: 836
<212> TYPE: DNA
<213> ORGANISM: Artificial sequence
<220> FEATURE:
<223> OTHER INFORMATION: E. coli W3110ATCC 27325

<400> SEQUENCE: 12
atgactatta cgctcacggg aaaatctcga acgtgagtt cctcaacctt gcggcgaagt      60
gcggtaggcg ggatgacggc attagcgttg tttgatttgc tcaagccaaa ttatgcgctg    120
gcgactcagg tagagtttac cgacccggaa attgttgctg agtacatcac gtatccttcg    180
ccaaatggtc acggcgaggt gcggggttat ctggtgaagc ccgcaaagat gagcggcaaa    240
acgccagccg tagtggtggt gcatgagaat cgtggactga atccgtatat cgaagatgtg    300
gcacggcgag tggcgaaggc ggggtatatc gccctggcac ctgacggctt aagttccgtt    360
ggaggttatc cgggaaatga tgataaaggt cgtgagctgc aacagcaggt tgatccaaca    420
aactgatgaa tgatttcttt gccgcaattg agtttatgca acgctatccg caagcgacag    480
gcaaagtggg tattaccgga ttttgctatg gcggtggcgt atcgaacgcg gcggctgtcg    540
cgtatccgga actggcctgc gcggtgccgt tttatggtcg tcaggcaccc actgccgatg    600
tggcgaagat tgaagcgcct ttactactcc acttcgcgga actggacacc cgaatcaacg    660
agggctggcc tgcttacgag gcggcgttga agccaataa taaggtttat gaggcgtata    720
tctatccggg ggtaatcac ggattccata atgattccac gccccgttat gacaaatctg     780
ccgccgatct tgcctggcaa aggacactga aatggttcga taaatatctc tcctga        836

<210> SEQ ID NO 13
<211> LENGTH: 20
<212> TYPE: DNA
<213> ORGANISM: Artificial sequence
<220> FEATURE:
<223> OTHER INFORMATION: The sequence is synthesized.

<400> SEQUENCE: 13
gcaacgggca atatgtctct                                                 20

<210> SEQ ID NO 14
<211> LENGTH: 30
<212> TYPE: DNA
<213> ORGANISM: Artificial sequence
<220> FEATURE:
```

<223> OTHER INFORMATION: The sequence is synthesized.

<400> SEQUENCE: 14
gctcaagacg ccaggtggtt ggtgattttg                30

<210> SEQ ID NO 15
<211> LENGTH: 31
<212> TYPE: DNA
<213> ORGANISM: Artificial sequence
<220> FEATURE:
<223> OTHER INFORMATION: The sequence is synthesized.

<400> SEQUENCE: 15
cgttacatcc gtgaagattg ccgaagtgga t               31

<210> SEQ ID NO 16
<211> LENGTH: 19
<212> TYPE: DNA
<213> ORGANISM: Artificial sequence
<220> FEATURE:
<223> OTHER INFORMATION: The sequence is synthesized.

<400> SEQUENCE: 16
agcacccaca gccactcat                            19

<210> SEQ ID NO 17
<211> LENGTH: 31
<212> TYPE: DNA
<213> ORGANISM: Artificial sequence
<220> FEATURE:
<223> OTHER INFORMATION: The sequence is synthesized.

<400> SEQUENCE: 17
aaccacctgg cgtcttgagc gattgtgtag g              31

<210> SEQ ID NO 18
<211> LENGTH: 31
<212> TYPE: DNA
<213> ORGANISM: Artificial sequence
<220> FEATURE:
<223> OTHER INFORMATION: The sequence is synthesized.

<400> SEQUENCE: 18
caatcttcac ggatgtaacg cactgagaag c              31

<210> SEQ ID NO 19
<211> LENGTH: 18
<212> TYPE: DNA
<213> ORGANISM: Artificial sequence
<220> FEATURE:
<223> OTHER INFORMATION: The sequence is synthesized.

<400> SEQUENCE: 19
tttccgccga cagggatt                             18

<210> SEQ ID NO 20
<211> LENGTH: 27
<212> TYPE: DNA
<213> ORGANISM: Artificial sequence
<220> FEATURE:
<223> OTHER INFORMATION: The sequence is synthesized.

<400> SEQUENCE: 20
gctcaagacg tttcgcggga atgggtg                   27

```
<210> SEQ ID NO 21
<211> LENGTH: 29
<212> TYPE: DNA
<213> ORGANISM: Artificial sequence
<220> FEATURE:
<223> OTHER INFORMATION: The sequence is synthesized.

<400> SEQUENCE: 21
cgttacatcc aagcggcgaa ggaagtgac                                     29

<210> SEQ ID NO 22
<211> LENGTH: 18
<212> TYPE: DNA
<213> ORGANISM: Artificial sequence
<220> FEATURE:
<223> OTHER INFORMATION: The sequence is synthesized.

<400> SEQUENCE: 22
atagaggcgt cgccagct                                                 18

<210> SEQ ID NO 23
<211> LENGTH: 31
<212> TYPE: DNA
<213> ORGANISM: Artificial sequence
<220> FEATURE:
<223> OTHER INFORMATION: The sequence is synthesized.

<400> SEQUENCE: 23
tcccgcgaaa cgtcttgagc gattgtgtag g                                  31

<210> SEQ ID NO 24
<211> LENGTH: 31
<212> TYPE: DNA
<213> ORGANISM: Artificial sequence
<220> FEATURE:
<223> OTHER INFORMATION: The sequence is synthesized.

<400> SEQUENCE: 24
ttcgccgctt ggatgtaacg cactgagaag c                                  31

<210> SEQ ID NO 25
<211> LENGTH: 20
<212> TYPE: DNA
<213> ORGANISM: Artificial sequence
<220> FEATURE:
<223> OTHER INFORMATION: The sequence is synthesized.

<400> SEQUENCE: 25
gctatgaatg cccaccgaat                                               20

<210> SEQ ID NO 26
<211> LENGTH: 32
<212> TYPE: DNA
<213> ORGANISM: Artificial sequence
<220> FEATURE:
<223> OTHER INFORMATION: The sequence is synthesized.

<400> SEQUENCE: 26
gctcaagacg cgtcattaaa ttcacgacgc tt                                 32

<210> SEQ ID NO 27
<211> LENGTH: 31
<212> TYPE: DNA
<213> ORGANISM: Artificial sequence
<220> FEATURE:
<223> OTHER INFORMATION: The sequence is synthesized.
```

<400> SEQUENCE: 27
cgttacatcc gaagctgtgg tatggctgtg c                           31

<210> SEQ ID NO 28
<211> LENGTH: 20
<212> TYPE: DNA
<213> ORGANISM: Artificial sequence
<220> FEATURE:
<223> OTHER INFORMATION: The sequence is synthesized.

<400> SEQUENCE: 28
ccatttggct tcatctaccg                                        20

<210> SEQ ID NO 29
<211> LENGTH: 41
<212> TYPE: DNA
<213> ORGANISM: Artificial sequence
<220> FEATURE:
<223> OTHER INFORMATION: The sequence is synthesized.

<400> SEQUENCE: 29
gtgaattcag gaaacagacc atgaacgaac aatattccgc a                41

<210> SEQ ID NO 30
<211> LENGTH: 31
<212> TYPE: DNA
<213> ORGANISM: Artificial sequence
<220> FEATURE:
<223> OTHER INFORMATION: The sequence is synthesized.

<400> SEQUENCE: 30
gcatggtacc aatatcgccg aatgtaacga c                           31

<210> SEQ ID NO 31
<211> LENGTH: 31
<212> TYPE: DNA
<213> ORGANISM: Artificial sequence
<220> FEATURE:
<223> OTHER INFORMATION: The sequence is synthesized.

<400> SEQUENCE: 31
tttaatgacg cgtcttgagc gattgtgtag g                           31

<210> SEQ ID NO 32
<211> LENGTH: 31
<212> TYPE: DNA
<213> ORGANISM: Artificial sequence
<220> FEATURE:
<223> OTHER INFORMATION: The sequence is synthesized.

<400> SEQUENCE: 32
ccacagcttc ggatgtaacg cactgagaag c                           31

<210> SEQ ID NO 33
<211> LENGTH: 23
<212> TYPE: DNA
<213> ORGANISM: Artificial sequence
<220> FEATURE:
<223> OTHER INFORMATION: The sequence is synthesized.

<400> SEQUENCE: 33
gagataattc acaagtgtgc gct                                    23

<210> SEQ ID NO 34
<211> LENGTH: 32

```
<212> TYPE: DNA
<213> ORGANISM: Artificial sequence
<220> FEATURE:
<223> OTHER INFORMATION: The sequence is synthesized.

<400> SEQUENCE: 34
tagtaaatcc catggtgtag ggccttctgt ag                              32

<210> SEQ ID NO 35
<211> LENGTH: 34
<212> TYPE: DNA
<213> ORGANISM: Artificial sequence
<220> FEATURE:
<223> OTHER INFORMATION: The sequence is synthesized.

<400> SEQUENCE: 35
ctacaccatg ggatttacta actggaagag gcac                            34

<210> SEQ ID NO 36
<211> LENGTH: 22
<212> TYPE: DNA
<213> ORGANISM: Artificial sequence
<220> FEATURE:
<223> OTHER INFORMATION: The sequence is synthesized.

<400> SEQUENCE: 36
ccggcacagt atcaaggtat tt                                         22

<210> SEQ ID NO 37
<211> LENGTH: 20
<212> TYPE: DNA
<213> ORGANISM: Artificial sequence
<220> FEATURE:
<223> OTHER INFORMATION: The sequence is synthesized.

<400> SEQUENCE: 37
tcaaattcag ccgatagcgg                                            20

<210> SEQ ID NO 38
<211> LENGTH: 30
<212> TYPE: DNA
<213> ORGANISM: Artificial sequence
<220> FEATURE:
<223> OTHER INFORMATION: The sequence is synthesized.

<400> SEQUENCE: 38
gaattatctc gctttccagt cgggaaacct                                 30

<210> SEQ ID NO 39
<211> LENGTH: 32
<212> TYPE: DNA
<213> ORGANISM: Artificial sequence
<220> FEATURE:
<223> OTHER INFORMATION: The sequence is synthesized.

<400> SEQUENCE: 39
cgttacatcc caggtagcag agcgggtaaa ct                              32

<210> SEQ ID NO 40
<211> LENGTH: 22
<212> TYPE: DNA
<213> ORGANISM: Artificial sequence
<220> FEATURE:
<223> OTHER INFORMATION: The sequence is synthesized.

<400> SEQUENCE: 40
```

-continued

```
ggatttcctt acgcgaaata cg                                              22
```

<210> SEQ ID NO 41
<211> LENGTH: 31
<212> TYPE: DNA
<213> ORGANISM: Artificial sequence
<220> FEATURE:
<223> OTHER INFORMATION: The sequence is synthesized.

<400> SEQUENCE: 41

```
actgtgccgg cgtcttgagc gattgtgtag g                                    31
```

<210> SEQ ID NO 42
<211> LENGTH: 31
<212> TYPE: DNA
<213> ORGANISM: Artificial sequence
<220> FEATURE:
<223> OTHER INFORMATION: The sequence is synthesized.

<400> SEQUENCE: 42

```
ctgctacctg ggatgtaacg cactgagaag c                                    31
```

<210> SEQ ID NO 43
<211> LENGTH: 91
<212> TYPE: DNA
<213> ORGANISM: Artificial sequence
<220> FEATURE:
<223> OTHER INFORMATION: The sequence is synthesized.

<400> SEQUENCE: 43

```
aataatcgtc taatacgact cactataggg tctagaaata attttgttta actttaagaa     60
ggagatatac catgaacgca accacagagc c                                    91
```

<210> SEQ ID NO 44
<211> LENGTH: 77
<212> TYPE: DNA
<213> ORGANISM: Artificial sequence
<220> FEATURE:
<223> OTHER INFORMATION: The sequence is synthesized.

<400> SEQUENCE: 44

```
gctcaagacg caaaaaaccc ctcaagaccc gtttagaggc cccaaggggt tatgctaggc     60
tgcgaacaac gaaagag                                                    77
```

<210> SEQ ID NO 45
<211> LENGTH: 19
<212> TYPE: DNA
<213> ORGANISM: Artificial sequence
<220> FEATURE:
<223> OTHER INFORMATION: The sequence is synthesized.

<400> SEQUENCE: 45

```
acagccagaa tgccagtgc                                                  19
```

<210> SEQ ID NO 46
<211> LENGTH: 32
<212> TYPE: DNA
<213> ORGANISM: Artificial sequence
<220> FEATURE:
<223> OTHER INFORMATION: The sequence is synthesized.

<400> SEQUENCE: 46

```
agtcgtatta gacgattatt cggcgttaca ct                                   32
```

```
<210> SEQ ID NO 47
<211> LENGTH: 27
<212> TYPE: DNA
<213> ORGANISM: Artificial sequence
<220> FEATURE:
<223> OTHER INFORMATION: The sequence is synthesized.

<400> SEQUENCE: 47
cgttacatcc tcggcgcttg attcacc                                       27

<210> SEQ ID NO 48
<211> LENGTH: 21
<212> TYPE: DNA
<213> ORGANISM: Artificial sequence
<220> FEATURE:
<223> OTHER INFORMATION: The sequence is synthesized.

<400> SEQUENCE: 48
cgtttgtccg ctcttcttac c                                             21

<210> SEQ ID NO 49
<211> LENGTH: 31
<212> TYPE: DNA
<213> ORGANISM: Artificial sequence
<220> FEATURE:
<223> OTHER INFORMATION: The sequence is synthesized.

<400> SEQUENCE: 49 gggtttttg cgtcttgagc gattgtgtag g                                   31

<210> SEQ ID NO 50
<211> LENGTH: 31
<212> TYPE: DNA
<213> ORGANISM: Artificial sequence
<220> FEATURE:
<223> OTHER INFORMATION: The sequence is synthesized.

<400> SEQUENCE: 50
caagcgccga ggatgtaacg cactgagaag c                                  31

<210> SEQ ID NO 51
<211> LENGTH: 89
<212> TYPE: DNA
<213> ORGANISM: Artificial sequence
<220> FEATURE:
<223> OTHER INFORMATION: The sequence is synthesized.

<400> SEQUENCE: 51
cgcttcaatc taatacgact cactataggg tctagaaata attttgttta actttaagaa   60
ggagatatac cacaaagatg gccctggtc                                     89

<210> SEQ ID NO 52
<211> LENGTH: 78
<212> TYPE: DNA
<213> ORGANISM: Artificial sequence
<220> FEATURE:
<223> OTHER INFORMATION: The sequence is synthesized.

<400> SEQUENCE: 52
gctcaagacg caaaaaccc ctcaagaccc gtttagaggc cccaaggggt tatgctagac    60
tgcgatggtg gtcattgt                                                 78

<210> SEQ ID NO 53
<211> LENGTH: 21
<212> TYPE: DNA
```

```
<213> ORGANISM: Artificial sequence
<220> FEATURE:
<223> OTHER INFORMATION: The sequence is synthesized.

<400> SEQUENCE: 53
gcgcaacgta gaacaggaat t                                               21

<210> SEQ ID NO 54
<211> LENGTH: 33
<212> TYPE: DNA
<213> ORGANISM: Artificial sequence
<220> FEATURE:
<223> OTHER INFORMATION: The sequence is synthesized.

<400> SEQUENCE: 54
agtcgtatta gattgaagcg cctttactac tcc                                  33

<210> SEQ ID NO 55
<211> LENGTH: 36
<212> TYPE: DNA
<213> ORGANISM: Artificial sequence
<220> FEATURE:
<223> OTHER INFORMATION: The sequence is synthesized.

<400> SEQUENCE: 55
cgttacatcc gtcatagtaa tccagcaact cttgtg                               36

<210> SEQ ID NO 56
<211> LENGTH: 22
<212> TYPE: DNA
<213> ORGANISM: Artificial sequence
<220> FEATURE:
<223> OTHER INFORMATION: The sequence is synthesized.

<400> SEQUENCE: 56
gagcaggtat ttacgtgaac cg                                              22

<210> SEQ ID NO 57
<211> LENGTH: 31
<212> TYPE: DNA
<213> ORGANISM: Artificial sequence
<220> FEATURE:
<223> OTHER INFORMATION: The sequence is synthesized.

<400> SEQUENCE: 57
gggttttttg cgtcttgagc gattgtgtag g                                    31

<210> SEQ ID NO 58
<211> LENGTH: 31
<212> TYPE: DNA
<213> ORGANISM: Artificial sequence
<220> FEATURE:
<223> OTHER INFORMATION: The sequence is synthesized.

<400> SEQUENCE: 58
ttactatgac ggatgtaacg cactgagaag c                                    31
```

XYLOSE-INDUCED GENETICALLY ENGINEERED BACTERIA USED FOR PRODUCING ECTOINE AND USE THEREOF

CROSS REFERENCE TO RELATED APPLICATIONS

This application is the national stage entry of International Application No. PCT/CN2017/088284, filed on Jun. 14, 2017, which is based upon and claims the priority of Chinese Patent No. 201710012845.6 filed on Jan. 9, 2017, and entitled "Xylose-Induced Genetically Engineered Bacteria Used for Producing Ectoine and Use Thereof", the entire of which are incorporated herein by reference.

SEQUENCE LISTING

The instant application contains a Sequence Listing which has been submitted in ASCII format via EFS-Web and is hereby incorporated by reference in its entirety. Said ASCII copy is named GBRSMJ023-POA_SequenceListing.txt, created on 08/22/2021 and is 30,217 bytes in size.

TECHNICAL FIELD

The present disclosure relates to the field of genetic engineering, especially relates to a xylose-induced genetically engineered bacteria used for producing ectoine as well as a construction method and use thereof.

BACKGROUND

Ectoine(1,4,5,6-tetrahydro-2-methyl-4-pyrimidinecarboxylic acid), which is a cyclic amino acid formed by intramolecular dehydration of N-acetylated diaminobutyric acid, it was used as an osmotic pressure compensating solute at the earliest time and was found in *Ectothiorhodospira halochloris* capable of carrying out photosynthesis. After years of research, ectoine also has been found in different halophilic fungi by scholars.

Recently, the osmotic protection function of ectoine and its application in other fields have drawn more and more attention. It has been found that ectoine can be used as a stabilizer to protect and stabilize enzymes, nucleic acids, DNA and other biological macromolecules against high temperature, drying, high osmotic pressure, freezing and other adverse environment. At present, ectoine has important uses in the fields of enzyme preparations, genetic engineering, medical treatment and cosmetics.

The use in the field of enzyme preparations: in the industrial processes, the physical and chemical conditions cannot be ensured to be the optimal condition of the enzyme reaction all the time, so that the enzyme preparations need to keep good activity in adverse environment such as different temperatures and salinities, and ectoine can help such protein macromolecules keep good activity under adverse environment.

The use in the field of genetic engineering: at present, the genes controlling the synthesis of ectoine have been expressed in tobacco to improve the salt tolerance of tobacco to a certain extent, although its expression level is relatively low; in addition, ectoine can reduce the Tm value of DNA; and for the template double-stranded DNA with high G+C content, the PCR amplification can be promoted by adding ectoine into the reaction system.

The use in the field of medical treatment: ectoine can not only be used as a protective agent of healthy cells during chemotherapy, but also have certain preventative effect on Alzheimer's disease and Parkinson's disease.

The use in the field of cosmetics: ectoine can be added into cosmetics as humectants for its osmotic protection function, so that the skin can be prevented from being dried and aged, and the damage of UV to the skin can be reduced.

At present, the production methods of ectoine include fermentation and enzyme catalysis. Thereinto, the halophilic microorganisms are widely used in the fermentation of ectoine for possessing the ectoine synthesis pathway. The ectoine synthesis pathway of halophilic bacteria is: oxaloacetic acid-aspartate-aspartate-β-semialdehyde-L-2,4-diaminobutyrate-Nγ-acetyl-diaminobutyrate-ectoine. Grammann et al. found a permeation regulation system from the *Halomonas elongate* which is different from the systems ever found, it contains three genes of ectA, ectB and ectC, these three genes are organized in an operon that controlled by a common promoter to express L-2,4-diaminobutyrate acetyltransferase, L-2,4-diaminobutyrate transaminase and ectoine synthase respectively.

In the present invention, the ectoine-synthesizing gene ectABC from a halophilic bacteria is introduced into an non-halophilic bacteria to reconstruct the ectoine synthesis pathway, resulting in the recombinant strain can synthesize ectoine by taking glucose as a raw material under the stress of moderate or low salt concentration.

In addition, in the present invention, the control gene iclR is also knocked out so as to break the glyoxylate cycle and increase the accumulation amount of the precursor oxylacetic acid; the homoserine-dehydrogenase I coding gene thrA is knocked out to prevent the metabolic shunt from L-aspartate-β-semialdehyde to threonine, lysine and methionine, and make more metabolic flux flow to the ectoine pathway; the expression intensity of gene ectABC is increased by replacing a promoter with a strong promoter T7, and the activity of the key enzyme is improved so as to increase the metabolic flux of the ectoine pathway; the expression level of lysC is increased by replacing with the strong promoter T7, and the feedback inhibition of lysine to the key enzyme aspartate kinase in the ectoine synthesis route is relieved, meanwhile, aspartate kinase is introduced to complement to over-accumulate ectoine; the RNA polymerase (T7RNAP) from T7 bacteriophage is promoted by the promoter of xylose transporter coding gene xylF (PxylF), moreover, the expression of exogenous genes are enhanced by the strong promoter T7.

SUMMARY OF THE INVENTION

One of technical schemes of the invention is to provide a genetically engineered bacteria *E. coli* ECT06 used for producing ectoine. The *E. coli* ECT06 is constructed as follows: heterologously expressing the ectABC gene cluster from *Halomonas elongata* on the *E. coli* chromosome to reconstruct the synthesis pathway of ectoine and build a non-plasmid system; using the promoter of xylose transporter coding gene xylF (PxylF) to control the RNA polymerase (T7RNAP) from T7 bacteriophage, and enhancing the expression of the target genes by strong promoter T7(Pt7).

The genetically engineered bacteria used for producing ectoine contains a ectABC gene from *Halomonas elongata* (CGMCC 1.6329) and promoted by promoter T7; gene deficiencies of gene thrA and gene iclR; a lysC gene from *Corynebacterium glutamicum* and controlled by promoter T7; a ppc gene promoted by promoter trc; and a RNA polymerase (T7RNAP) from T7 bacteriophage and promoted by the promoter PxylF which is the promoter of xylose transporter coding gene xylF.

The nucleotide sequence of the ectABC gene is a sequence shown in a sequence table as SEQ ID NO: 1.

The nucleotide sequence of the lysC gene is a sequence shown in a sequence table as SEQ ID NO: 2.

The nucleotide sequence of the thrA gene is a sequence shown in a sequence table as SEQ ID NO: 3.

The nucleotide sequence of the iclR gene is a sequence shown in a sequence table as SEQ ID NO: 4.

The nucleotide sequence of the promoter T7 is a sequence shown in a sequence table as SEQ ID NO: 5.

The nucleotide sequence of the terminator T7 is a sequence shown in a sequence table as SEQ ID NO: 6.

The nucleotide sequence of the promoter trc is a sequence shown in a sequence table as SEQ ID NO: 7.

The nucleotide sequence of the ppc gene is a sequence shown in a sequence table as SEQ ID NO: 8.

The nucleotide sequence of the PxylF is a sequence shown in a sequence table as SEQ ID NO: 9.

The nucleotide sequence of the T7RNAP is a sequence shown in a sequence table as SEQ ID NO: 10.

The host cell of the genetically engineered bacteria used for producing ectoine is $E.\ coli$ W3110 (ATCC 27325).

Another technical scheme of the invention is to provide a construction method of the genetically engineered bacteria used for producing ectoine, specifically comprises the following steps:

(1) knocking out the thrA and iclR genes from the starting strain $E.\ coli$ W3110 (ATCC 27325);

(2) replacing the promoter of ppc gene with promoter trc;

(3) expressing the T7 RNA polymerase: a junction fragment of the promoter of xylose transporter coding gene xylF (PxylF) and T7 RNA polymerase (T7RNAP) is constructed and expressed;

(4) constructing the metabolic pathway from aspartate to ectoine:

① constructing a gene fragment T7-ectABC by ligating promoter T7 and ectABC gene, and expressing it;

② constructing a gene fragment T7-lysC by ligating promoter T7 and lysC gene, and expressing it.

Another technical scheme of the invention is to provide a production method of ectoine by using the genetically engineered bacteria above mentioned, details are as follows:

The shake-flask fermentation, which specifically comprises the following steps:

(1) seed culture: the slant cultured cells are inoculated into a seed culture medium, and cultured at 37° C., 200 rpm for 7 hours;

(2) shake-flask fermentation: the seed liquid is inoculated into a fermentation medium according to a inoculum size of 10-15%, and cultured for 20-28 hours at 37° C. and 200 rpm; the pH is maintained to be 7.2 by supplementing $NH_4OH$, and a 60% (m/v) glucose solution is used for maintaining the fermentation(the phenol red is used as an indicator, and that the color of the fermentation broth changes no longer means sugar deficiency, and then 1-2 ml of 60% glucose solution is added), the expression of the target gene is induced by adding 60% (m/v) xylose solution (final concentration of xylose in the fermentation broth is 5-15 g/L) at the initial stage of fermentation, and the fermentation period is 20-28 h.

The yield of ectoine reached 12-16 g/L after 20-28 h fermentation in shake flask.

The seed medium: sucrose 20-30 g/L, $(NH_4)_2SO_4$ 1-5 g/L, $KH_2PO_4$ 1-5 g/L, $MgSO_4.7H_2O$ 1-2 g/L, yeast extract powder 5-10 g/L, corn steep liquor 1-3 mL/L, $FeSO_4.7H_2O$ 1-3 mg/L, $MnSO_4.H_2O$ 1-3 mg/L, the rest is water, pH7.0.

The fermentation medium: glucose 20-40 g/L, $(NH_4)_2SO_4$ 1-3 g/L, $KH_2PO_4$ 1-3 g/L, $MgSO_4.7H_2O$ 1-2 g/L, yeast extract powder 0.1-0.3 g/L, corn steep liquor 1-2 mL/L, $FeSO_4.7H_2O$ 80-100 mg/L, $MnSO_4.7H_2O$ 80-100 mg/L, the rest is water, pH7.0.

The fermentor fermentation, which specifically comprises the following steps:

(1) slant culture: a loop of thallus is scraped off from the strain deposit tube stored in −80° C., and spread evenly on the agar slant culture medium to culture at 37° C. for 15-18 hours, and then transferred into a second-generation agar slant to culture for 12 hours;

(2) seed culture: proper amount of sterile water is added into the agar slant to make a bacterial suspension, then inoculated the bacterial suspension into a seed medium and cultured to a cell dry weight of 5-6 g/L, during the period the pH is stabilized to be about 7.0, the temperature is kept constantly at 36° C., and the dissolved oxygen is 25-35%.

(3) fermentor fermentation: the seed liquid is inoculated into a fermentation medium according to a inoculum size of 15-20%, and cultured for 24-40 hours, during the period the pH is stabilized to be about 7.0, the temperature is kept constantly at 36° C., and the dissolved oxygen is 25-35%;

The expression of the target gene is induced by adding xylose solution to the fermentation medium with a final concentration of 5-15 g/L at the initial stage, and when the glucose in the medium is exhausted, a 80% glucose solution is added to maintain the glucose concentration in the fermentation medium at 0-2 g/L, and the fermentation period is 24-40 hours.

The yield of ectoine reached 35-50 g/L after 24-40 hours fermentation in a 5 L fermentor.

The agar slant culture medium: sucrose 1-3 g/L, tryptone 5-10 g/L, beef extract 5-10 g/L, yeast extract 2-5 g/L, NaCl 2-5 g/L, agar 15-30 g/L, the rest is water, pH 7.0-7.2, carrying out high-pressure steam sterilization at 115° C. for 15 minutes.

The seed medium: glucose 15-30 g/L, yeast extract 5-10 g/L, tryptone 5-10 g/L, $KH_2PO_4$ 5-15 g/L, $MgSO_4.7H_2O$ 2-5 g/L, $FeSO_4.7H_2O$ 5-15 mg/L, $MnSO_4.H_2O$ 5-15 mg/L, VB1 1-3 mg/L, VH 0.1-1 mg/L, defoamer 2 drops, the rest is water, pH 7.0-7.2, carrying out high-pressure steam sterilization at 115° C. for 15 minutes.

The fermentation medium: glucose 15-25 g/L, yeast extract 1-5 g/L, tryptone 1-5 g/L, sodium citrate 0.1-1 g/L, $KH_2PO_4$ 1-5 g/L, $MgSO_4.7H_2O$ 0.1-1 g/L, $FeSO_4.7H_2O$ 80-100 mg/L, $MnSO_4.H_2O$ 80-100 mg/L, VB1 0.5-1 mg/L, VH 0.1-0.5 mg/L, defoamer 2 drops, the rest is water, pH 7.0-7.2, carrying out high-pressure steam sterilization at 115° C. for 15 minutes.

The Beneficial Effects

1. After a series of modification, the genetically engineered bacteria used for producing ectoine disclosed in this invention has an enhanced metabolic flux of glucose to L-aspartate-β-semialdehyde, and the genetically engineered bacteria can directly utilize glucose as a raw material to produce ectoine; the yield of ectoine reached 12-16 g/L after 20-28 h fermentation in shake flasks, and reached 35-50 g/L after fermentation in a 5 L fermentor for 24-40 h.

Figure 2:
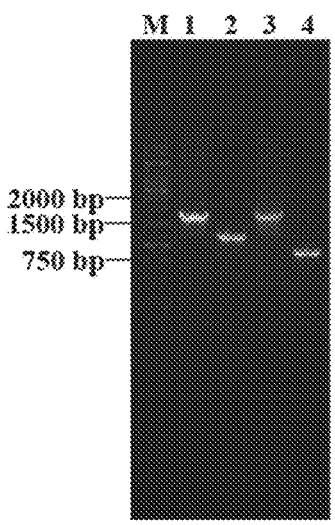

Wherein, M: Marker, 1: upstream homologous arm, 2: chloramphenicol resistance gene fragment, 3: downstream homologous arm, 4: overlapping fragment; 5: PCR fragment obtained by using original genomic DNA as template; 6: PCR fragment obtained by using genomic DNA with deletion of gene thrA as template, 7: PCR fragment obtained by using genomic DNA with deletion of chloramphenicol resistance gene as template;

FIG. 2: Deletion and verification of iclR gene

Figure 3:
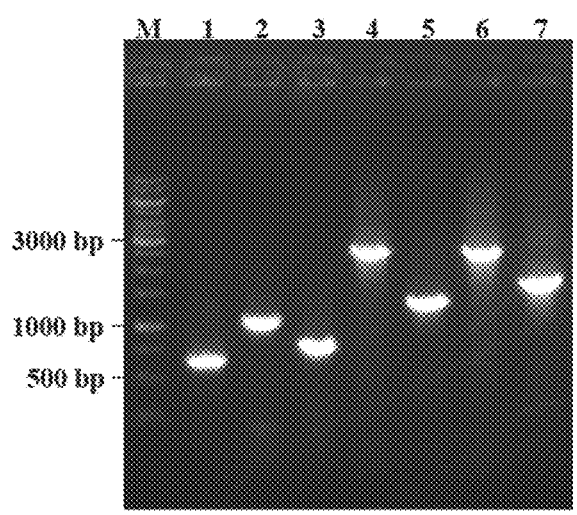

Wherein, M: Marker, 1: iclR gene deletion fragment; 2: PCR fragment obtained by using original genomic DNA as template, 3: PCR fragment obtained by using genomic DNA with deletion of iclR as template, 4: PCR fragment obtained by using genomic DNA with deletion of chloramphenicol resistance gene as template;

FIG. 3: Replacement of $P_{ppc}$ with $P_{trc}$ and verification

Figure 4:
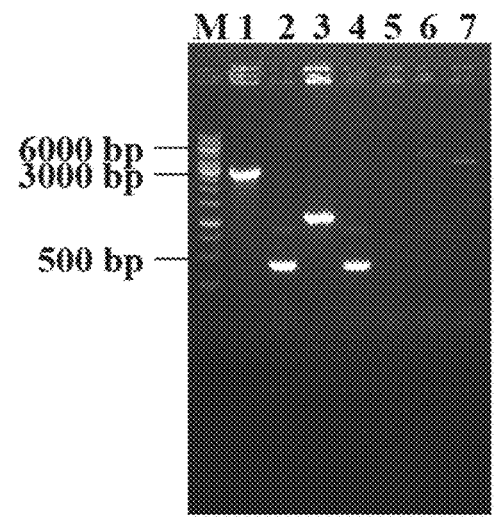

Wherein, M: Marker, 1: upstream homologous arm, 2: chloramphenicol resistance gene fragment, 3: downstream homologous arm, 4: promoter replacing fragment; 5: PCR fragment obtained before promoter replacement, 6: PCR fragment obtained after promoter replacement, 7: PCR fragment obtained by using genomic DNA with deletion of Chloramphenicol resistance gene as template;

FIG. 4: Construction and PCR verification of PxylF-T7RNAP integrated fragment

Figure 5:
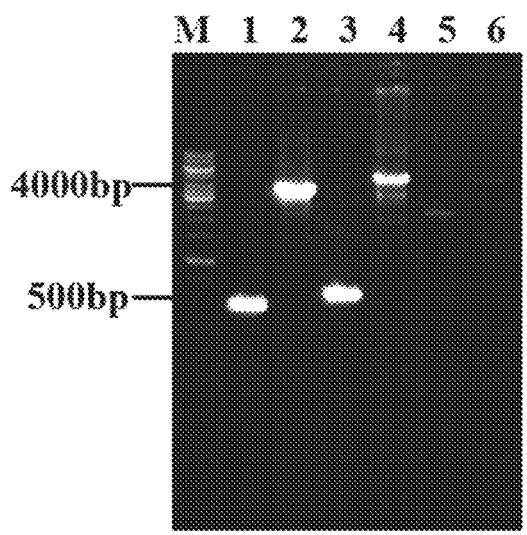

Wherein, M: Marker, 1: PxylF-T7RNAP overlapping fragment, 2: upstream homologous arm, 3: chloramphenicol resistance gene fragment, 4: downstream homologous arm, 5: PxylF-T7RNAP integrated fragment; 6: PCR fragment obtained after replacing lacZ with PxylF-T7RNAP integrated fragment, 7: PCR fragment obtained by using genomic DNA with deletion of chloramphenicol resistance gene as template;

FIG. 5: Construction and PCR verification of T7-ectABC integrated fragment

Figure 6:
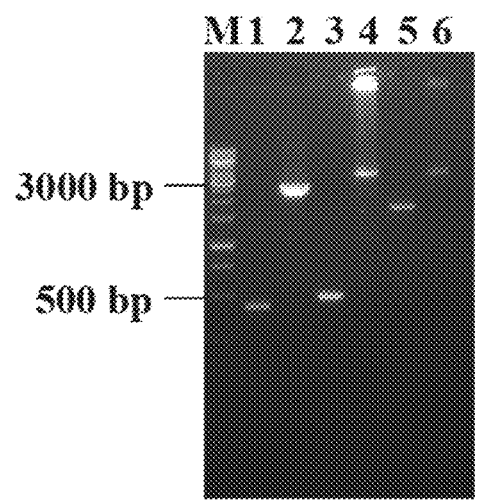

Wherein, M: Marker, 1: upstream homologous arm, 2: overlapping fragment of T7-ectABC and chloramphenicol resistance gene, 3: downstream homologous arm, 4: T7-ectABC integrated fragment; 5: the original gene fragment; 6: PCR fragment obtained after replacing ybeM gene with T7-ectABC integrated fragment;

FIG. 6: Construction and PCR verification of T7-lysC integrated fragment

Figure 7:
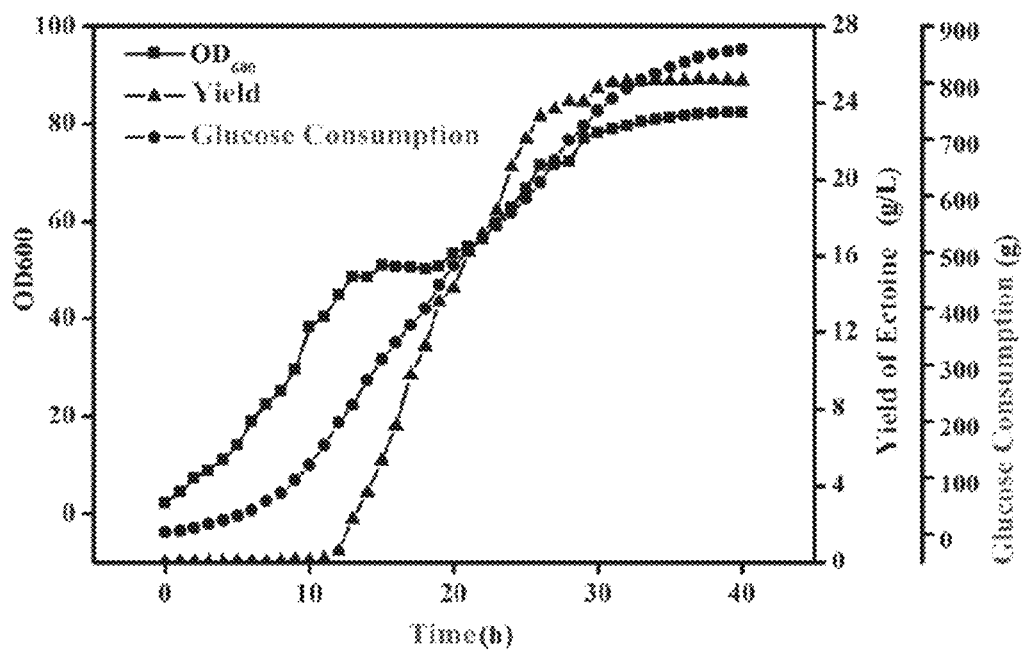

Wherein, M: Marker, 1: upstream homologous arm, 2: overlapping fragment of T7-lysC and chloramphenicol resistance gene, 3: downstream homologous arm, 4: T7-lysC integrated fragment; 5: the original gene fragment, 6: PCR fragment of genomic DNA after replacing yghX gene with T7-lysC integrated fragment;

FIG. 7: The fermentation process curve of the control strain in example 4.

Figure 8:
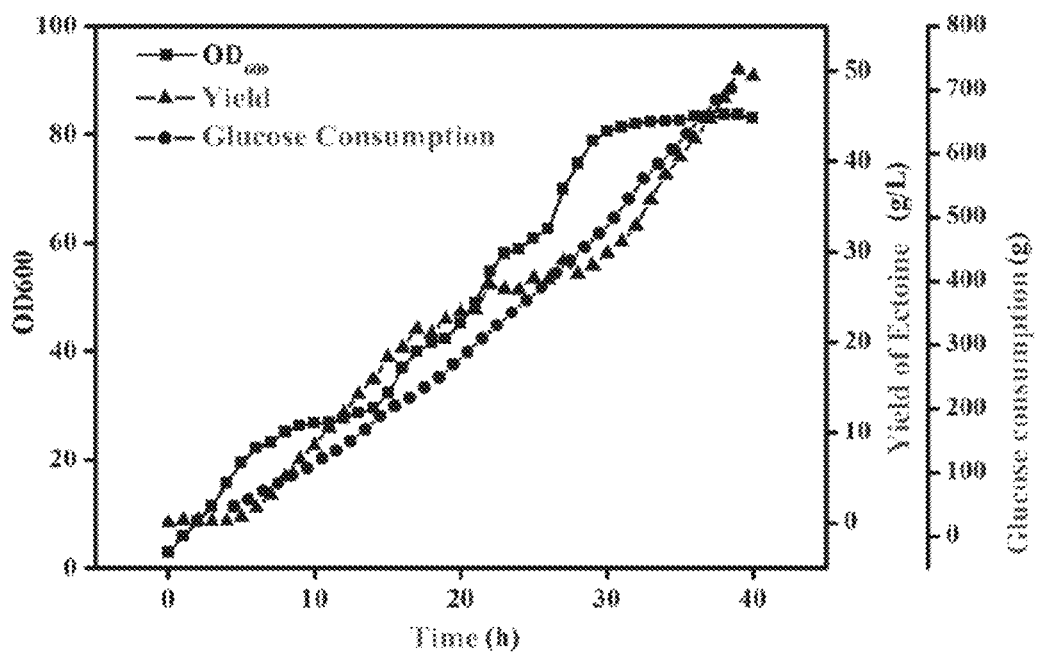

FIG. 8: The fermentation process curve of the test strain in example 4.

DETAILED DESCRIPTION

Example 1. Construction of Strain E. coli ECT 06

(1) Deletions of thrA Gene and iclR Gene

Figure 1:
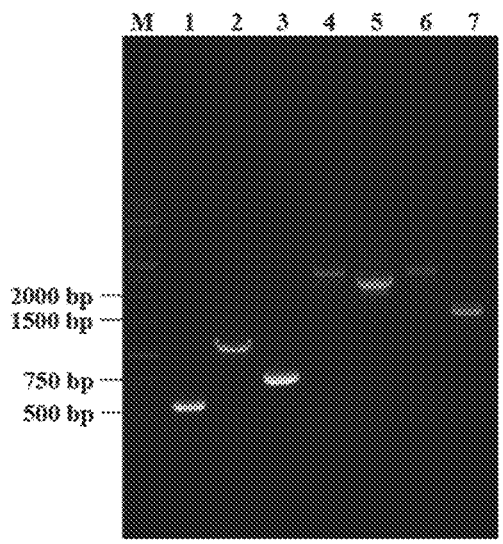
FIG. 1: Deletion and verification of the thrA gene

Deletions of thrA gene and iclR gene were performed using the Red recombination system:

① the upstream and downstream homologous arms of the thrA gene were obtained by PCR amplification using the genomic DNA of E. coli W3110 (ATCC 27325) as a template and upstream homologous arm primers (thrA-up-1, thrA-up-2) and downstream homologous arm primers (thrA-down-1, thrA-down-2) as primers which were designed according to the gene sequence of thrA gene;

② a chloramphenicol resistance gene fragment was amplified by PCR using plasmid pKD3 as a template and $Cm^r$-thrA-up, $Cm^r$-thrA-down as primers;

③ a thrA gene deletion fragment was amplified by overlapping PCR using the amplified fragments obtained in step ① and ② as templates, and the thrA gene deletion fragment was composed of upstream and downstream homologous arms of the thrA gene and the chloramphenicol resistance gene fragment;

④ transforming the thrA gene deletion fragment into the E. coli W3110 harboring plasmid pKD46 to obtain positive transformants, and then the E. coli ECT01 that a bacterium with thrA gene deletion was obtained by eliminating the chloramphenicol resistance gene fragment from the positive transformants; (the verification of thrA gene deletion by electrophoresis shown in FIG. 1: the upstream homologous arm was about 500 bp, the downstream homologous arm was about 700 bp, the chloramphenicol resistance gene fragment was about 1080 bp, the thrA gene deletion fragment was about 2500 bp; the original gene was about 2000 bp, PCR fragment obtained by PCR amplification after deletion of chloramphenicol resistance gene was about 1500 bp, the electrophoretic bands were consistent with the designed size, which proved that the thrA gene was successfully deleted).

Deletion of gene iclR: a E. coli ECT02 was obtained by deleting iclR gene from E. coli ECT01 using the same method above mentioned (the primers of upstream homologous arm: iclR-up-1, iclR-up-2; the primers of downstream homologous arm: iclR-down-1, iclR-down-2; the primers of chloramphenicol resistance gene fragment: $Cm^r$-iclR-up, $Cm^r$-iclR-down). (the deletion of iclR gene was verified by electrophoresis shown in FIG. 2: the upstream homologous arm was about 500 bp, the downstream homologous arm was about 500 bp, the chloramphenicol resistance gene fragment was about 1080 bp, the thrA gene deletion fragment was about 1700 bp; the original gene was about 1200 bp, PCR fragment obtained by PCR amplication after deletion of chloramphenicol resistance gene was about 800 bp, the electrophoretic bands were consistent with the designed size, which proved that the iclR gene was successfully deleted).

(2) Replacement the Promoter of Ppc Gene with Promoter Trc

① the upstream and downstream homologous arms of the the promoter of ppc were amplified by PCR using the genomic DNA of E. coli W3110 (ATCC 27325) as a template and the upstream homologous arm primers ($p_{ppc}$-up-1, $p_{ppc}$-up-2) and downstream homologous arm primers ($p_{ppc}$-down-1, $p_{ppc}$-down-2) as primers which were designed according to the gene sequence of ppc gene; the upstream homologous arm was located upstream of the promoter of ppc, and the downstream homologous arm was located in front of the ppc structure gene for 600 bp;

② amplifying the promoter trc from plasmid pTrc99a(the forward primer: $p_{trc}$-up; the reverse primer: per-down);

③ a chloramphenicol resistance gene fragment was amplified by PCR using plasmid pKD3 as a template and $Cm^r$-ppc-up, $Cm^r$-ppc-down as primers;

④ a promoter of ppc gene replacing fragment was amplified by overlapping PCR using the amplified fragments obtained in step ①, ② and ③ as templates, and the promoter of ppc gene replacing fragment was composed of upstream and downstream homologous arms of the promoter of ppc gene, promoter trc and the chloramphenicol resistance gene fragment;

⑤ E. coli ECT03, the promoter of ppc of which was replaced with promoter trc, was obtained by transforming the promoter of ppc gene replacing fragment into the E. coli ECT02 and then eliminating the chloramphenicol resistance gene fragment; (the replacing of the promoter of ppc gene with promoter trc was verified by electrophoresis shown in FIG. 3: the upstream homologous arm was about 700 bp, the downstream homologous arm was about 800 bp, the chloramphenicol resistance gene fragment is about 1080 bp, the replacing fragment was about 2300 bp, the original gene was about 1300 bp, PCR fragment obtained by PCR amplification after deletion of chloramphenicol resistance gene was about 1500 bp. The electrophoretic bands were consistent with the designed size, which proved that the promoter was successfully replaced).

(3) Expression of T7 RNA Polymerase (T7RNAP)

① a promoter PxylF of xylose transporter coding gene xylF was amplified by PCR using the genomic DNA of E. coli W3110 (ATCC 27325) as a template and PxylF-up, PxylF-down as primers which were designed according to the gene sequence of xylF;

② a T7RNAP fragment was amplified by PCR using the genomic DNA of E. coli BL21(DE3) as a template and T7RNAP-up, T7RNAP-down as primers which were designed according to the gene sequence of T7RNAP;

③ a chloramphenicol resistance gene fragment was amplified by PCR using plasmid pKD3 as a template and Cm$^r$-lacZ-up, Cm$^r$-lacZ-down as primers;

④ the upstream and downstream homologous arms of the lacZ gene were amplified by PCR using the genomic DNA of E. coli W3110(ATCC27325) as a template and the upstream homologous arm primers(lacZ-up-1, lacZ-up-2), downstream homologous arm primers(lacZ-down-1, lacZ-down-2) as primers which were designed according to the gene sequence of lacZ gene; the upstream and downstream homologous arms were both located inside the lacZ gene;

⑤ an integrated fragment PxylF-T7RNAP was amplified by overlapping PCR using the amplified fragments obtained in step ①, ②, ③ and ④ as templates, and the integrated fragment PxylF-T7RNAP was composed of upstream and downstream homologous arms of lacZ gene, the chloramphenicol resistance gene fragment, the promoter PxylF and the T7RNAP fragment;

⑥ E. coli ECT04 was obtained by transforming the integrated fragment PxylF-T7RNAP into the E. coli ECT03 harboring plasmid pKD46 and eliminating the chloramphenicol resistance gene fragment, in which the lacZ gene was replaced with T7RNAP promoted by a promoter PxylF; (the expression of PxylF-T7RNAP integrated fragment was verified by electrophoresis shown in FIG. 4: the upstream homologous arm was about 451 bp, the downstream homologous arm was about 456 bp, the chloramphenicol resistance gene fragment was about 1024 bp, the overlapping fragment PxylF-T7RNAP was about 3000 bp, the integrated fragment PxylF-T7RNAP was about 5000 bp; the original gene fragment was about 3700 bp, PCR fragment obtained by PCR amplication after deletion of chloramphenicol resistance gene was about 4000 bp. The electrophoretic bands were consistent with the designed size, which proved that the integrated fragment PxylF-T7RNAP was successfully integrated).

(4) Construction of Metabolic Pathway from Aspartate to Ectoine

① an ectABC gene was amplified by PCR using the genomic DNA of Halomonas elongata (CGMCC 1.6329) as a template and ectABC-up, ectABC-down as primers which were designed according to the gene sequence of ectABC, and a T7-ectABC fragment was obtained by PCR using primers which were performed by adding promoter T7 and terminator T7 to the 5' and 3' ends of the ectABC fragment amplification primers;

② a chloramphenicol resistance gene fragment was amplified by PCR using plasmid pKD3 as a template and Cm$^r$-ybeM-up, Cm$^r$-ybeM-down as primers;

③ the upstream and downstream homologous arms of the ybeM gene were amplified by PCR using the genomic DNA of E. coli W3110(ATCC27325) as a template and the upstream homologous arm primers(ybeM-up-1, ybeM-up-2), downstream homologous arm primers(ybeM-down-1 ybeM-down-2) as primers which were designed according to the gene sequence of ybeM gene; the upstream and downstream homologous arms were both located inside the ybeM gene; the nucleotide sequence of the ybeM gene was a sequence shown in a sequence table as SEQ ID NO: 11;

④ an integrated fragment T7-ectABC was amplified by overlapping PCR using the amplified fragments obtained in step ①, ② and ③ as templates, and the integrated fragment T7-ectABC was composed of upstream and downstream homologous arms of ybeM gene, the promoter T7, the chloramphenicol resistance gene fragment, ectABC fragment and the terminator T7;

⑤ a E. coli ECT05 was obtained by transforming the integrated fragment T7-ectABC into the E. coli ECT04 and eliminating the chloramphenicol resistance gene fragment, in which the ybeM gene was replaced by a promoter T7 promoted ectABC; (the integration of integrated fragment T7-ectABC was verified by electrophoresis shown in FIG. 5: the upstream homologous arm was about 488 bp, the downstream homologous arm was about 645 bp, the chloramphenicol resistance gene fragment was about 1024 bp, the T7-ectABC was about 2500 bp; the integrated fragment T7-ectABC was about 4500 bp, the original gene fragment was about 2000 bp, the electrophoretic bands were consistent with the designed size, which proved that the integrated fragment T7-ectABC was successfully integrated).

(5) Introducing of lysC Gene from Corynebacterium glutamicum

① a lysC gene was amplified by PCR using the genomic DNA of Corynebacterium glutamicum ATCC13032 as a template and lysC-up, lysC-down as primers which were designed according to the gene sequence of lysC, and a T7-lysC fragment was obtained by PCR using primers which were performed by adding promoter T7 and terminator T7 to the 5' and 3' ends of the lysC fragment amplification primers;

② a chloramphenicol resistance gene fragment was amplified by PCR using plasmid pKD3 as a template and Cm$^r$-yghX-up, Cm$^r$-yghX-down as primers;

③ the upstream and downstream homologous arms of the yghX gene were amplified by PCR using the genomic DNA of E. coli W3110(ATCC27325) as a template and the upstream homologous arm primers(yghX-up-1,yghX-up-2), downstream homologous arm primers(yghX-down-1, yghX-down-2) as primers which were designed according to the gene sequence of yghX gene; the upstream and downstream homologous arms were both located inside the yghX gene; the nucleotide sequence of the yghX gene was a sequence shown in a sequence table as SEQ ID NO: 12;

④ an integrated fragment T7-lysC was amplified by overlapping PCR using the amplified fragments obtained in step ①, ② and ③ as templates, and the integrated fragment T7-lysC was composed of upstream and downstream homologous arms of yghX gene, the promoter T7, the chloramphenicol resistance gene fragment, lysC gene fragment and the terminator T7;

⑤ a *E. coli* ECT06 was obtained by transforming the integrated fragment T7-lysC into the *E. coli* ECT05 and eliminating the chloramphenicol resistance gene fragment, in which the yghX gene was replaced by a promoter T7 promoted lysC; (the integration of integrated fragment T7-lysC was verified by electrophoresis shown in FIG. 6: the upstream homologous arm was about 418 bp, the downstream homologous arm was about 480 bp, the chloramphenicol resistance gene fragment was about 1024 bp, the T7-lysC was about 1500 bp, the integrated fragment T7-lysC was about 3500 bp, the original gene fragment was about 1732 bp. As can be seen in FIG. 6, the electrophoretic bands were consistent with the designed size, which proves that the T7-lysC was successfully integrated).

The primers used in the experiment are shown in the following table:

| Primers | Sequence (5'-3') | SEQ ID NO: |
|---|---|---|
| thrA-up-1 | GCAACGGGCAATATGTCTCT | 13 |
| thrA-up-2 | GCTCAAGACGCCAGGTGGTTGGTGATTTTG | 14 |
| thrA-down-1 | CGTTACATCCGTGAAGATTGCCGAAGTGGAT | 15 |
| thrA-down-2 | AGCACCCACAGCCACTCAT | 16 |
| Cm$^r$-thrA-up | AACCACCTGGCGTCTTGAGCGATTGTGTAGG | 17 |
| Cm$^r$-thrA-down | CAATCTTCACGGATGTAACGCACTGAGAAGC | 18 |
| iclR-up-1 | TTTCCGCCGACAGGGATT | 19 |
| iclR-up-2 | GCTCAAGACGTTTCGCGGGAATGGGTG | 20 |
| iclR-down-1 | CGTTACATCCAAGCGGCGAAGGAAGTGAC | 21 |
| iclR-down-2 | ATAGAGGCGTCGCCAGCT | 22 |
| Cm$^r$-iclR-up | TCCCGCGAAACGTCTTGAGCGATTGTGTAGG | 23 |
| Cm$^r$-iclR-down | TTCGCCGCTTGGATGTAACGCACTGAGAAGC | 24 |
| P$_{ppc}$-up-1 | GCTATGAATGCCCACCGAAT | 25 |
| P$_{ppc}$-up-2 | GCTCAAGACGCGTCATTAAATTCACGACGCTT | 26 |
| P$_{ppc}$-down-1 | CGTTACATCCGAAGCTGTGGTATGGCTGTGC | 27 |
| P$_{ppc}$-down-2 | CCATTTGGCTTCATCTACCG | 28 |
| P$_{trc}$-up | GTGAATTCAGGAAACAGACCATGAACGAACA ATATTCCGCA | 29 |
| ptrc-down | GCATGGTACCAATATCGCCGAATGTAACGAC | 30 |
| Cm$^r$-ppc-up | TTTAATGACGCGTCTTGAGCGATTGTGTAGG | 31 |
| Cm$^r$-ppc-down | CCACAGCTTCGGATGTAACGCACTGAGAAGC | 32 |
| PxylF-up | GAGATAATTCACAAGTGTGCGCT | 33 |
| PxylF-down | TAGTAAATCCCATGGTGTAGGGCCTTCTGTAG | 34 |
| T7RNAP-up | CTACACCATGGGATTTACTAACTGGAAGAGGCAC | 35 |
| T7RNAP-down | CCGGCACAGTATCAAGGTATTT | 36 |
| lacZ-up-1 | TCAAATTCAGCCGATAGCGG | 37 |
| lacZ-up-2 | GAATTATCTCGCTTTCCAGTCGGGAAACCT | 38 |
| lacZ-down-1 | CGTTACATCCCAGGTAGCAGAGCGGGTAAACT | 39 |
| lacZ-down-2 | GGATTTCCTTACGCGAAATACG | 40 |
| Cm$^r$-lacZ-up | ACTGTGCCGGCGTCTTGAGCGATTGTGTAGG | 41 |
| Cm$^r$-lacZ-down | CTGCTACCTGGGATGTAACGCACTGAGAAGC | 42 |
| ectABC-up | AATAATCGTCTAATACGACTCACTATAGGGTCTAGAAATAATT TTGTTTAACTTTAAGAAGGAGATATACCATGAACGCAACCACA GAGCC | 43 |

-continued

| Primers | Sequence (5'-3') | SEQ ID NO: |
| --- | --- | --- |
| ectABC-down | GCTCAAGACGCAAAAAACCCCTCAAGACCCGTTT AGAGGCCCCAAGGGGTTATGCTAGGCTGCGAACA ACGAAAGAG | 44 |
| ybeM-up-1 | ACAGCCAGAATGCCAGTGC | 45 |
| ybeM-up-2 | AGTCGTATTAGACGATTATTCGGCGTTACACT | 46 |
| ybeM-down-1 | CGTTACATCCTCGGCGCTTGATTCACC | 47 |
| ybeM-down-2 | CGTTTGTCCGCTCTTCTTACC | 48 |
| Cm$^r$-ybeM-up | GGGTTTTTTGCGTCTTGAGCGATTGTGTAGG | 49 |
| Cm$^r$-ybeM-down | CAAGCGCCGAGGATGTAACGCACTGAGAAGC | 50 |
| lysC-up | CGCTTCAATCTAATACGACTCACTATAGGGTCTAGA AATAATTTTGTTTAACTTTAAGAAGGAGATATACCA CAAAGATGGCCCTGGTC | 51 |
| lysC-down | GCTCAAGACGCAAAAAACCCCTCAAGACCCGTTT AGAGGCCCCAAGGGGTTATGCTAGACTGCGATGGT GGTCATTGT | 52 |
| yghX-up-1 | GCGCAACGTAGAACAGGAATT | 53 |
| yghX-up-2 | AGTCGTATTAGATTGAAGCGCCTTTACTACTCC | 54 |
| yghX-down-1 | CGTTACATCCGTCATAGTAATCCAGCAACTCTTGTG | 55 |
| yghX-down-2 | GAGCAGGTATTTACGTGAACCG | 56 |
| Cm$^r$-yghX-up | GGGTTTTTTGCGTCTTGAGCGATTGTGTAGG | 57 |
| Cm$^r$-yghX-down | TTACTATGACGGATGTAACGCACTGAGAAGC | 58 |

Example 2. Shake-Flask Fermentation Experiment

The strain E. coli ECT 06 constructed in example 1 was used as a production strain to produce ectonie by fermentation.

(1) Seed culture: a loop of thallus was inoculated into a 500 mL erlenmeyer flask with 30 mL seed medium, and cultured for 7 hours at 37° C. and 200 rpm.

(2) Shake-flask fermentation: the seed solution was inoculated into a 500 mL baffled shake flask with 30 mL fermentation medium according to a inoculum size of 15%, and cultured for 28 hours at 37° C. and 200 rpm; the phenol red was used as an indicator, $NH_4OH$ was supplemented through a microsyringe to kept the pH at 7.2, and 60% (m/v) glucose solution was used for maintaining the fermentation (the phenol red was used as an indicator, and it will be seen as sugar deficiency when the color of the fermentation broth no longer changed, and then 2 ml of 60% glucose solution can be added), the expression of the target gene was induced by adding 60% (m/v) xylose solution (final concentration of xylose in the fermentation broth was 15 g/L) at the initial stage of fermentation, and the fermentation period was 28 h.

(3) Collection of the fermentation broth: the fermentation broth was centrifuged at 13000 rpm, collecting the supernate phase and detecting the content of ectoine. The result showed the yield of ectoine reached 16 g/L after 28 h fermentation in shake flask.

(4) Detection method:
the supernate was diluted 200 times with deionized water and filtered by a 0.22 μm microfiltration membrane, the resulting sample was to be detected; the detection was performed by an UltiMate 3000 (Thermo Scientific) high performance liquid chromatograph using a TSK-GEL C18 chromatographic column with 2% acetonitrile at a flow rate was 1 mL/min as the mobile phase, the column temperature was 30° C., and 20 μL sample was injected by using a trace sample injection needle, the ultraviolet detection wavelength was 210 nm, and the retention time was about 2.953 min.

The seed medium: sucrose 30 g/L, $(NH_4)_2SO_4$ 5 g/L, $KH_2PO_4$ 5 g/L, $MgSO_4 \cdot 7H_2O$ 2 g/L, yeast extract powder 10 g/L, corn steep liquor 3 mL/L, $FeSO_4 \cdot 7H_2O$ 3 mg/L, $MnSO_4 \cdot H_2O$ 3 mg/L, the rest is water, pH7.0.

The fermentation medium: glucose 40 g/L, $(NH_4)_2SO_4$ 3 g/L, $KH_2PO_4$ 3 g/L, $MgSO_4 \cdot 7H_2O$ 2 g/L, yeast extract powder 0.3 g/L, corn steep liquor 2 mL/L, $FeSO_4 \cdot 7H_2O$ 100 mg/L, $MnSO_4 \cdot 7H_2O$ 100 mg/L, the rest is water, pH7.0.

Example 3. Shake-Flask Fermentation Experiment

The strain E. coli ECT06 constructed in example 1 was used to produce ectonie.

(1) Seed culture: a loop of thallus was inoculated into a 500 mL erlenmeyer flask with 30 mL seed medium, and cultured for 7 hours at 37° C. and 200 rpm.

(2) Shake-flask fermentation: the seed solution was inoculated into a 500 mL baffled shake flask with 30 mL fermentation medium according to a inoculum size of 10%, and cultured for 20 hours at 37° C. and 200 rpm; the phenol red was used as an indicator, and the pH was kept at 7.2 by supplementing $NH_4OH$, the 60% (m/v) glucose solution was used for maintaining the fermentation(the phenol red was used as an indicator, and the color of the fermentation broth no longer changed meaning sugar deficiency, and then 1 mL of 60% glucose solution was added), the expression of the target gene was induced by adding 60% (m/v) xylose solution (final concentration of xylose in the fermentation broth was 5 g/L) at the initial stage of fermentation, and the fermentation period was 20 h.

(3) Collection of the fermentation broth: the fermentation broth was centrifuged at 13000 rpm, collecting the supernate phase and detecting the content of ectoine. The result showed the yield of ectoine reached 12 g/L after 20 h fermentation in shake flask.

(4) Detection method:

the supernate was diluted 200 times with deionized water and filtered by a 0.22 μm microfiltration membrane, the resulting sample was to be detected; the detection of ectoine was performed by using an UltiMate 3000 (Thermo Scientific) high performance liquid chromatograph, and 20 μL sample was injected with a trace sample injection needle, the chromatographic column was a TSK-GEL C18 chromatographic column, and the column temperature was 30° C., the mobile phase was 2% acetonitrile, the flow rate was 1 mL/min, the ultraviolet detection wavelength was 210 nm, and the retention time was about 2.953 min.

The seed medium: sucrose 20 g/L, $(NH_4)_2SO_4$ 1 g/L, $KH_2PO_4$ 1 g/L, $MgSO_4.7H_2O$ 1 g/L, yeast extract powder 5 g/L, corn steep liquor 1 mL/L, $FeSO_4.7H_2O$ 1 mg/L, $MnSO_4.H_2O$ 1 mg/L, the rest is water, pH7.0;

The fermentation medium: glucose 20 g/L, $(NH_4)_2SO_4$ 1 g/L, $KH_2PO_4$ 1 g/L, $MgSO_4.7H_2O$ 1 g/L, yeast extract powder 0.1 g/L, corn steep liquor 1 mL/L, $FeSO_4.7H_2O$ 80 mg/L, $MnSO_4.7H_2O$ 80 mg/L, the rest is water, pH7.0.

Example 4. Fermentation Experiment in a 5 L Fermentor

Test strain: the strain *E. coli* ECT06 constructed in example 1.

Control strain: the strain *E. coli* ECT06 constructed in the Chinese patent application "A Genetically Engineered Bacteria Used for Producing Ectoine as well as the Construction Method and Use Thereof", application number: 201510410080.2.

Both of the two strains above mentioned were adopted to execute the fermentor fermentation experiment respectively under the same condition to produce ectoine, and the method specifically comprises the following steps:

(1) slant culture: a loop of thallus was scraped off from the strain deposit tube stored in −80° C., and spread evenly on the agar slant culture medium to culture for 15 hours, then transferred into a second-generation agar slant to culture for 12 hours.

(2) seed culture: proper amount of sterile water was added into four tubes of agar slant to make a bacterial suspension, then inoculated into a 7.5 L fermentor with 2 L seed medium and cultured to a cell dry weight of 6 g/L, during the period the pH was stabilized to be about 7.0 by automated addition of $NH_4OH$, the temperature was kept constantly at 36° C. by temperature electrode, and the dissolved oxygen was 25-35% by variation of the stirrer speed and aeration rate.

(3) fermentor fermentation: the seed liquid was inoculated into a fermentation medium according to a inoculum size of 20%, and cultured for 40 hours, during the period the pH was stabilized to be about 7.0, the temperature was kept constantly at 36° C., and the dissolved oxygen was 25-35%; and when the glucose in the medium was exhausted, a 80% (m/v) glucose solution was added to maintain the glucose concentration in the fermentation medium at 0-2 g/L;

Xylose was added to the fermentation medium at the initial fermentation stage of the test strain with a 15 g/L of final concentration in the fermentation broth to induce the expression of the target gene (there is no addition of xylose in the fermentation process of the control strain).

The slant culture medium: sucrose 3 g/L, tryptone 10 g/L, beef extract 10 g/L, yeast extract 5 g/L, NaCl 5 g/L, agar 30 g/L, the rest is water, pH 7.0-7.2, carrying out high-pressure steam sterilization at 115° C. for 15 minutes.

The seed medium: glucose 30 g/L, yeast extract 10 g/L, tryptone 10 g/L, $KH_2PO_4$ 15 g/L, $MgSO_4.7H_2O$ 5 g/L, $FeSO_4.7H_2O$ 15 mg/L, $MnSO_4.H_2O$ 15 mg/L, VB1 3 mg/L, VH 1 mg/L, defoamer 2 drops, the rest is water, pH 7.0-7.2, carrying out high-pressure steam sterilization at 115° C. for 15 minutes.

The fermentation medium: glucose 25 g/L, yeast extract 5 g/L, tryptone 5 g/L, sodium citrate 1 g/L, $KH_2PO_4$ 5 g/L, $MgSO_4.7H_2O$ 1 g/L, $FeSO_4.7H_2O$ 100 mg/L, $MnSO_4.H_2O$ 100 mg/L, VB1 1 mg/L, VH 0.5 mg/L, defoamer 2 drops, the rest is water, pH 7.0-7.2, carrying out high-pressure steam sterilization at 115° C. for 15 minutes.

The results are shown in the following table, FIG. 7 and FIG. 8:

| Strains | $OD_{600}$ | Yield of Ectoine (g/L) | Substrate Conversion (%) | Fermentation Period (h) | specific production rate (g/L/h) |
|---|---|---|---|---|---|
| Control Strain | 78.9 | 25.2 | 9.8 | 40 | 0.63 |
| Test Strain | 83.0 | 50.1 | 27.8 | 40 | 1.25 |

Example 5. Fermentation Experiment in a 5 L Fermentor

The strain *E. coli* ECT06 constructed in example 1 was used as the producing strain to produce ectoine, and the method specifically comprises the following steps:

(1) slant culture: a loop of thallus was scraped off from the stain deposit tube stored in −80° C., and spread evenly on the agar slant culture medium to culture 18 hours, then transferred into a second-generation agar slant to culture 12 hours.

(2) seed culture: proper amount of sterile water was added into four tubes of agar slant to make a bacterial suspension, then inoculated into a 7.5 L fermentor with 2 L seed medium and cultured to a cell dry weight of 5 g/L, during the period the pH was stabilized to be about 7.0 by automated addition of $NH_4OH$, the temperature was kept constantly at 36° C. by temperature electrode, and the dissolved oxygen was 25-35% by variation of the stirrer speed and aeration rate.

(3) fermentor fermentation: the seed liquid was inoculated into a fermentation medium according to an inoculum size of 15%, and cultured for 24 hours, during the period the pH was stabilized to be about 7.0, the temperature was kept at 36° C., and the dissolved oxygen was 25-35%;

the expression of the target gene was induced by adding 5 g/L xylose to the fermentation medium at the initial fermentation stage, and when the glucose in the medium was consumed, a 80% (m/v) glucose solution was added by a mode of fed-batch to maintain the glucose concentration in the fermentation medium at 0-2 g/L.

The concentration of ectoine in the fermentation broth reached 35 g/L after 24 h culture.

The slant culture: sucrose 1 g/L, tryptone 5 g/L, beef extract 5 g/L, yeast extract 2 g/L, NaCl 2 g/L, agar 15 g/L, the rest is water, pH 7.0-7.2, carrying out high-pressure steam sterilization at 115° C. for 15 minutes.

The seed medium: glucose 15 g/L, yeast extract 5 g/L, tryptone 5 g/L, KH$_2$PO$_4$ 5 g/L, MgSO$_4$.7H$_2$O 2 g/L, FeSO$_4$.7H$_2$O 5 mg/L, MnSO$_4$.H$_2$O 5 mg/L, VB1 1 mg/L, VH 0.1 mg/L, defoamer 2 drops, the rest is water, pH 7.0-7.2, carrying out high-pressure steam sterilization at 115° C. for 15 minutes.

The fermentation medium: glucose 15 g/L, yeast extract 1 g/L, tryptone 1 g/L, sodium citrate 0.1 g/L, KH$_2$PO$_4$ 1 g/L, MgSO$_4$.7H$_2$O 0.1 g/L, FeSO$_4$.H$_2$O 80 mg/L, MnSO$_4$.H$_2$O 80 mg/L, VB1 0.5 mg/L, VH 0.1 mg/L, defoamer 2 drops, the rest is water, pH 7.0-7.2, carrying out high-pressure steam sterilization at 115° C. for 15 minutes.

What is claimed is:

1. A genetically engineered bacterium used for producing ectoine, wherein the genetically engineered bacterium is *E. coli* ECT06 comprising: *E. coli* W3110 modified to have an ectABC gene promoted by a promoter T7 and from *Halomonas elongata*; deletions of only thrA and iclR genes; a lysC gene promoted by a promoter T7 and from *Corynebacterium glutamicum*; a ppc gene promoted by a promoter trc; and a gene encoding a RNA polymerase from T7 bacteriophage and promoted by a promoter PxylF of xylose transporter coding gene xylF.

2. The genetically engineered bacterium used for producing ectoine according to claim 1, wherein a starting host cell strain of the genetically engineered bacteria is *E. coli* W3110 deposited under deposit number ATCC 27325.

3. The genetically engineered bacterium used for producing ectoine according to claim 1, wherein the deposit number of the *Halomonas elongata* is CGMCC No. 1.6329.

4. The genetically engineered bacterium used for producing ectoine according to claim 1, wherein
- the nucleotide sequence of the ectABC gene comprises SEQ ID NO: 1;
- the nucleotide sequence of the lysC gene comprises SEQ ID NO: 2;
- the nucleotide sequence of the thrA gene comprises SEQ ID NO: 3;
- the nucleotide sequence of the iclR gene comprises SEQ ID NO: 4;
- the nucleotide sequence of the promoter T7 comprises SEQ ID NO: 5;
- the nucleotide sequence of the promoter trc comprises SEQ ID NO: 7;
- the nucleotide sequence of the ppc gene comprises SEQ ID NO: 8;
- the nucleotide sequence of the PxylF comprises SEQ ID NO: 9; and
- the nucleotide sequence of the gene encoding the RNA polymerase from T7 bacteriophage comprises SEQ ID NO: 10.

5. A construction method of the genetically engineered bacterium used for producing ectoine of claim 1, comprising the following steps:
(1) knocking out thrA and iclR genes of a starting strain of *E. coli* W3110;
(2) replacing a promoter of ppc gene of the starting strain with promoter trc;
(3) constructing a gene fragment by ligating the promoter PxylF of xylose transporter coding gene xylF and the gene encoding T7 RNA polymerase, and transforming into the *E. coli* W3110; and
(4) constructing a metabolic pathway from aspartate to ectoine by
① constructing a gene fragment T7-ectABC by ligating promoter T7 and ectABC gene, and transforming into the *E. coli* W3110; and
② constructing a gene fragment T7-lysC by ligating promoter T7 and lysC gene, and transforming into the *E. coli* W3110.

6. A method of using the genetically engineered bacterium according to claim 1, for production of ectoine by shake-flask fermentation comprising:
(1) inoculating slant cultured cells of the genetically engineered bacterium into a seed culture medium, and culturing for 7 hours at 37° C. and 200 rpm to produce a seed liquid;
(2) inoculating the seed liquid into a fermentation medium according to an inoculum size of 10-15%, and culturing for 20-28 hours at 37° C. and 200 rpm; maintaining the pH to be 7.2, adding a 60% (m/v) glucose solution to maintain the fermentation, adding a xylose solution to the fermentation medium to a final concentration of 5-15 g/L in the fermentation medium to induce expression of the ectABC gene, the lysC gene or the gene encoding T7 RNA polymerase.

7. The method according to claim 6, wherein
the seed culture medium comprises sucrose 20-30 g/L, $(NH_4)_2SO_4$ 1-5 g/L, $KH_2PO_4$ 1-g/L, $MgSO_4.7H_2O$ 1-2 g/L, yeast extract powder 5-10 g/L, corn steep liquor 1-3 mL/L, $FeSO_4.7H_2O$ 1-3 mg/L, $MnSO_4.H_2O$ 1-3 mg/L, the rest is water, pH7.0; and
the fermentation medium comprises glucose 20-40 g/L, $(NH_4)_2SO_4$ 1-3 g/L, $KH_2PO_4$ 1-3 g/L, $MgSO_4.7H_2O$ 1-2 g/L, yeast extract powder 0.1-0.3 g/L, corn steep liquor 1-2 mL/L, $FeSO_4.7H_2O$ 80-100 mg/L, $MnSO_4.7H_2O$ 80-100 mg/L, the rest is water, pH7.0.

8. A method of using the genetically engineered bacterium according to claim 1, for production of ectoine by fermentor fermentation comprising the following steps:
(1) scraping a loop of thallus comprising the genetically engineered bacterium from a tube stored in −80° C., and spreading the loop evenly on an agar slant culture medium, culturing the agar slant culture medium at 37° C. for 15-18 hours, and then transferring into a second-generation agar slant culture medium and culturing the second-generation agar slant culture medium for 12 hours;
(2) adding sterile water into the second-generation agar slant culture medium to make a bacterial suspension, then inoculating the bacterial suspension into a seed medium and culturing to a cell dry weight of 5-6 g/L wherein pH is stabilized at 7.0, temperature is kept constant at 36° C., and dissolved oxygen is 25-35% to produce a seed liquid;
(3) inoculating the seed liquid into a fermentation medium in a fermentor according to a inoculum size of 15-20%, and culturing for 24-40 hours wherein pH is stabilized at 7.0, temperature is kept constant at 36° C., and dissolved oxygen is 25-35%; and
(4) adding during the culturing in (3) a xylose solution to the fermentation medium to a concentration of 5-15 g/L in the fermentation medium to induce expression of the ectABC gene, the lysC gene or the gene encoding T7 RNA polymerase, and adding a 80% (m/v) glucose solution to maintain the glucose concentration in the fermentation medium at 0-2 g/L after an initial amount of glucose in the fermentation medium is consumed.

9. The method according to claim 8, wherein
each agar slant culture medium comprises sucrose 1-3 g/L, Tryptone 5-10 g/L, beef extract 5-10 g/L, yeast extract 2-5 g/L, NaCl 2-5 g/L, agar 15-30 g/L, the rest is water, pH 7.0-7.2, that has been high-pressure steam sterilized at 115° C. for 15 minutes;
the seed medium comprises glucose 15-30 g/L, yeast Extract 5-10 g/L, Tryptone 5-10 g/L, $KH_2PO_4$ 5-15 g/L, $MgSO_4.7H_2O$ 2-5 g/L, $FeSO_4.7H_2O$ 5-15 mg/L, $MnSO_4.7H_2O$ 5-15 mg/L, VB1 1-3 mg/L, VH 0.1-1 mg/L, defoamer, the rest is water, pH 7.0-7.2, that has been high-pressure steam sterilized at 115° C. for 15 minutes; and
the fermentation medium comprises glucose 15-25 g/L, yeast extract 1-5 g/L, Tryptone 1-5 g/L, sodium citrate 0.1-1 g/L, $KH_2PO_4$ 1-5 g/L, $MgSO_4.7H_2O$ 0.1-1 g/L, $FeSO_4.7H_2O$ 80-100 mg/L, $MnSO_4.H_2O$ 80-100 mg/L, VB1 0.5-1 mg/L, VH 0.1-0.5 mg/L, defoamer, the rest is water, pH 7.0-7.2, that has been high-pressure steam sterilized at 115° C. for 15 minutes.

\* \* \* \* \*